United States Patent
He et al.

(10) Patent No.: US 8,865,724 B2
(45) Date of Patent: Oct. 21, 2014

(54) PREPARATION OF 2-METHYL-4-AMINO-5(SUBSTITUTED-1H-1,2,3-TRIAZOLYL) METHYLPYRIMIDINE DERIVATIVES AND MICROBICIDAL ACTIVITY THEREOF

(71) Applicant: Central China Normal University, Hubei (CN)

(72) Inventors: Hongwu He, Hubei (CN); Junbo He, Hubei (CN); Fang Wang, Hubei (CN); Xiaoguo Wang, Hubei (CN); Xiaosong Tan, Hubei (CN); Hao Peng, Hubei (CN)

(73) Assignee: Central China Normal University, Wuhan, Hubei (CN)

( * ) Notice: Subject to any disclaimer, the term of this patent is extended or adjusted under 35 U.S.C. 154(b) by 0 days.

(21) Appl. No.: 14/204,225

(22) Filed: Mar. 11, 2014

(65) Prior Publication Data

US 2014/0194625 A1  Jul. 10, 2014

Related U.S. Application Data

(63) Continuation of application No. PCT/CN2012/081261, filed on Sep. 11, 2012.

(30) Foreign Application Priority Data

Sep. 13, 2011 (CN) .......................... 2011 1 0268908
Sep. 10, 2012 (CN) .......................... 2012 1 0331267

(51) Int. Cl.
*C07D 403/06* (2006.01)
*A01N 43/647* (2006.01)

(52) U.S. Cl.
CPC ............ *C07D 403/06* (2013.01); *A01N 43/647* (2013.01)
USPC ........................................ 514/256; 544/328

(58) Field of Classification Search
USPC .......................................... 544/328; 514/256
See application file for complete search history.

(56) References Cited

PUBLICATIONS

Ren Yanliang et al., "Structure-based rational design of novel hit compounds for pyruvate dehydrogenase multienzyme complex E1 components from *Escherichia coli*", Bioorganic & Medicinal Chemistry, Oct. 19, 2011, vol. 19, pp. 7501-7506, especially the p. 7502, compounds 3a-3e in scheme 1.

He Junbo et al., "Design, synthesis and biological evaluation of novel 2-methylpyrimidine-4-ylamine derivatives as inhibitors of *Escherichia coli* pyruvate dehydrogenase complex E1", Bioorganic & Medicinal Chemistry, Jan. 21, 2012, vol. 20, pp. 1665-1670, especially the p. 1667, compounds 3a-3o, 5a and 5b in table 1.

Erixon Karl M. et al., "Inhibition of pyrophosphate decarboxylase from *Z. mobilis* by novel analogues of thiamine pyrophosphate: investigating pyrophosphate mimics", Chem. Commun., Dec. 8, 2006, 2007, pp. 960-962, especially the p. 960, compounds 11-16 in scheme 1.

State Intellectual Property Office of the P. R. China (ISA/CN), "International Search Report", Dec. 13, 2012, China.

*Primary Examiner* — Bruck Kifle
(74) *Attorney, Agent, or Firm* — Tim Tingkang Xia, Esq.; Morris, Manning & Martin, LLP

(57) ABSTRACT

Disclosed is a derivative of 2-methyl-4-amino-5-(substituted-1H-1,2,3-triazol)methylpyrimidine of general formula I and microbicidal activity thereof. In the formula, R1 represents hydrogen, I; X represents O or NH; Y represents phenyl of substituted phenyl, benzoyl or substituted benzoyl, phenyloxyacetyl or substituted phenyloxyacetyl; the substituents on the phenyl rings which Y involves are: H, halogen, nitro, cyano, CF3, C1~4 alkyl, methoxyl, C1~2 carboxyl or carboxylic ester groups; any position of phenyl rings can be mono- or multi-substituted by identical or different substituents. The compound has a significant inhibition effect on cucumber bacterial angular leaf spot, tomato bacterial leaf spot, cucumber brown blot, cucumber downy mildew, rice sheath blight, *Gibberella saubinetii*, *Alternaria solani*, *Botrytis cinerea*, *Alternaria alternate* and *Colletotrichum orbiculare* and it can be used as an effective ingredient of microbicides.

4 Claims, No Drawings

PREPARATION OF 2-METHYL-4-AMINO-5(SUBSTITUTED-1H-1,2,3-TRIAZOLYL) METHYLPYRIMIDINE DERIVATIVES AND MICROBICIDAL ACTIVITY THEREOF

CROSS-REFERENCE TO RELATED APPLICATIONS

This application is a continuation application of International Patent Application No. PCT/CN2012/081261, filed Sep. 11, 2012, which itself claims the priority to Chinese Patent Application Nos. 201110268908.7 and 201210331267.X, filed Sep. 13, 2011 and Sep. 10, 2012, respectively, in the State Intellectual Property Office of P.R. China, which are hereby incorporated herein in their entireties by reference.

Some references, if any, which may include patents, patent applications and various publications, may be cited and discussed in the description of this invention. The citation and/or discussion of such references, if any, is provided merely to clarify the description of the present invention and is not an admission that any such reference is "prior art" to the invention described herein. All references listed, cited and/or discussed in this specification are incorporated herein by reference in their entireties and to the same extent as if each reference was individually incorporated by reference.

FIELD OF THE INVENTION

The present invention relates to preparation of 2-methyl-4-amino-5-(substituted-1H-1,2,3-triazolyl)methylpyrimidine derivatives and microbicidal activity thereof.

BACKGROUND OF THE INVENTION

Current development and study of new pesticides are focused on searching and discovery of pesticidal active compounds that not only have new structures but also have new targets. In the process of regulation and control of energy metabolism, conversion of pyruvic acid from glycolysis into acetyl CoA as substrate for tricarboxylic acid cycle is a very important stage. This conversion is catalyzed by pyruvic dehydrogenases. If the pyruvate dehydrogenases are inhibited, pyruvic acid would be reduced into lactic acid instead of being converted into acetyl CoA. Accordingly, the source of acetyl CoA required in tricarboxylic acid cycle is limited, resulting in reduced yield of Adenosine Triphosphate (ATP), resulting in energy metabolic disturbance and tissue blocking, and under serious conditions resulting in death. Based on this biochemical feature, the pyruvic dehydrogenase complex may be used as a target of pesticides. Currently, there are reports about inhibitors of pyruvic dehydrogenases. For example, thiamine pyrophosphate analogs A-1 and A-2 are reported as highly active inhibitors against pyruvic dehydrogenases in microbes.

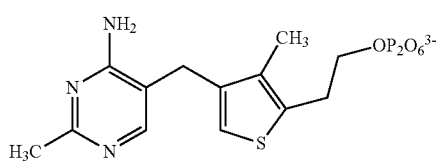

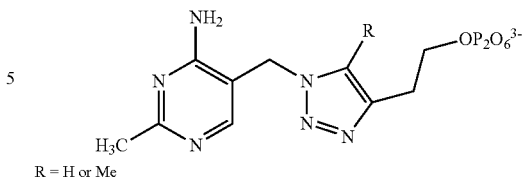

R = H or Me

Although the thiamine pyrophosphate analogs A are a group of highly active inhibitors against pyruvic dehydrogenases in microbes, these compounds are complex in structure, difficult in synthesis and have low value in application, especially have not yet shown application value in agriculture. Accordingly, with pyruvic dehydrogenases in microbes as target, novel highly active inhibitors are designed and synthesized by applicant of this invention. Specifically, novel structural compounds are discovered as microbicide useful in agriculture. Those novel compounds are significant and valuable in study and development of novel highly active microbicide.

SUMMARY OF THE INVENTION

In one aspect, the present invention is directed to novel triazolyl methylpyrimidine derivatives. Specifically, the present invention is directed to a novel 2-methyl-4-amino-5-(substituted-1H-1,2,3-triazolyl)methylpyrimidine derivative having microbicidal activity, and preparation and use thereof. The compounds not only have high inhibition on pyruvic dehydrogenases in microbes, but also have superior microbicidal activity.

In one embodiment, the compound of the present invention has a structural of general formula I:

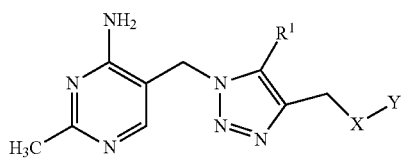

In the formula I, $R^1$ represents hydrogen or iodine (I);

X represents O or NH;

Y represents phenyl or substituted phenyl, benzoyl or substituted benzoyl, phenoxyacetyl or substituted phenoxyacetyl. A substituent on the benzene ring involved in Y is H, halogen, nitro, cyano, $CF_3$, $C_{1-4}$ alkyl, methoxy, $C_{1-2}$ carboxy or carboxylate. The substituents on the benzene ring of Y are mono- or multi-substituted at any position of the benzene ring, and the substituents can be the same or different.

The compounds of formula I includes 2-methyl-4-amino-5-((4-substituted phenoxymethyl-5-substituted)-1H-1,2,3-triazol-1-yl)methylpyrimidine compounds represented by general formula I-1;

N-((1-((2-methyl-4-aminopyrimidin-5-yl)methyl)-1H-1,2,3-triazol-4-yl)methyl)substituted benzoyl ester(amine) compounds represented by general formula I-2; and N-((1-((2-methyl-4-aminopyrimidin-5-yl)methyl)-1H-1,2,3-triazol-4-yl)methyl)-2-(substituted phenoxy) acetyl ester(amine) compounds represented by general formula I-3.

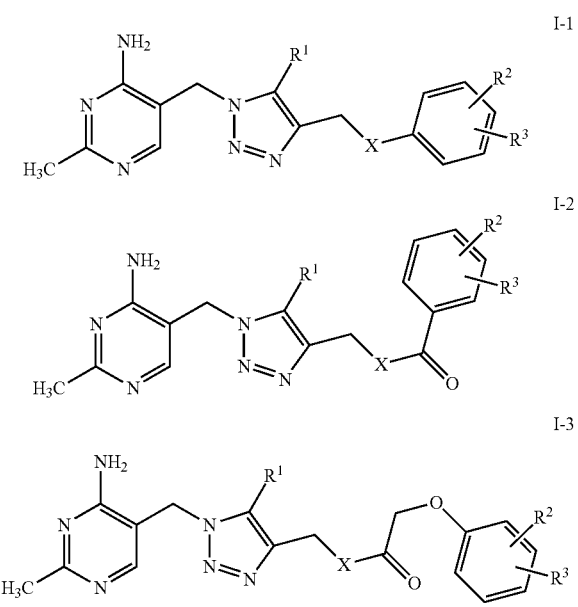

The structures of the three new compounds of general formulas I-1, I-2 and I-3 provided by the present invention have not been reported in any patent or literature. The structures of formulas I-1, I-2 and I-3 are defined respectively as follows.

In the 2-methyl-4-amino-5-((4-substituted phenoxymethyl-5-substituted)-1H-1,2,3-triazol-1-yl)methylpyrimidine compounds represented by general formula I-1 above, X is oxygen; $R^1$ is defined as in general formula I; $R^2$ is H, halogen, nitro or $C_{1-4}$ alkyl; $R^3$ is H, halogen, nitro, cyano, $CF_3$, $C_{1-4}$ alkyl, methoxy, $C_{1-2}$ carboxy or carboxylate; and positions of $R^2$ and $R^3$ are exchangeable.

In the 2-methyl-4-amino-5-(substituted-1H-1,2,3-triazolyl)methylpyrimidine derivatives represented by general formula I-2 above, X is defined as in general formula I; $R^1$ is defined as in general formula I; $R^2$ is H, halogen or nitro; $R^3$ is H, halogen, nitro or $C_{1-4}$ alkyl; and positions of $R^2$ and $R^3$ are exchangeable.

In the 2-methyl-4-amino-5-(substituted-1H-1,2,3-triazolyl)methylpyrimidine derivatives represented by general formula I-3 above, X is defined as in general formula I; $R^1$ represents hydrogen; $R^2$ is H, halogen, nitro, $CF_3$ or $C_{1-4}$ alkyl; $R^3$ is H, halogen, nitro, $C_{1-4}$ alkyl or methoxy; and positions of $R^2$ and $R^3$ are exchangeable.

The compounds of general formula I above according to the present invention have significantly controlling effects on bacterial spot of cucumber, tomato bacterial leaf spot, *corynespora* leaf spot of cucumber, downy mildew of cucumber, rice sheath blight disease, wheat scab, early blight of tomato, gray mold of cucumber, tobacco brown spot and anthracnose of cucumber, and may be used as microbicide.

Methods for preparing 2-methyl-4-amino-5-((4-substituted phenoxymethyl-5-substituted)-1H-1,2,3-triazol-1-yl)methylpyrimidine compounds represented by general formula I-1: a ring-closing reaction of the compounds of general formula II with substituted phenoxypropyne in the presence of catalyst or catalyst and organic base at temperature of −10° C. to 80° C. for 1-24 hours. Method A:

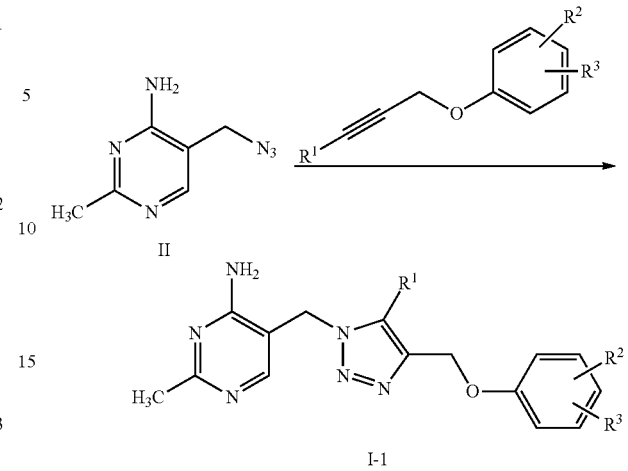

wherein $R^1$, $R^2$ and $R^3$ are defined as in general formula I-1 above.

In the reaction above, a molar ratio of the compounds of formula II to substituted phenoxypropyne to catalyst to organic base is 1:0.8-1.2:0.01-0.15:2. The organic solvent used as the reaction solvent is dichloromethane, dioxane, dichloroethane, acetone, tert-butyl alcohol:water, benzene, ethyl acetate, tetrahydrofuran, acetonitrile, N,N-dimethyl formamide or dimethyl sulfoxide. The catalyst is CuI, CuBr(PPh$_3$)$_3$, CuSO$_4$.5H$_2$O:sodium ascorbate, CuBr or Cu(OAc)$_2$. The organic base is triethylamine, diisopropylethylamine, pyridine or piperidine.

Method for preparing N-((1-((2-methyl-4-aminopyrimidin-5-yl)methyl)-1H-1,2,3-triazol-4-yl)methyl)substituted benzoyl ester(amine) compounds represented by general formula I-2: ring-closing reaction of the compounds of general formula II with substituted benzoyloxy(amino)propyne in the presence of catalyst or catalyst and organic base at temperature of −10° C. to 80° C. and catalytic conditions for 1-24 hours. Method B:

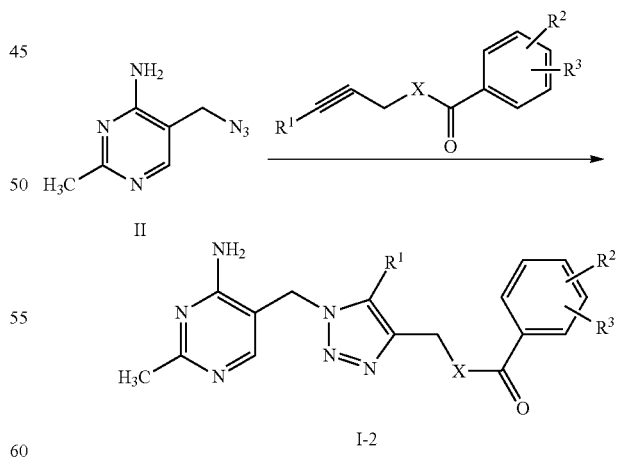

wherein X, $R^2$ and $R^3$ are defined as in general formula I-2 above.

In the reaction above, a molar ratio of the compounds of formula II to substituted benzoyloxypropyne to catalyst to organic base is 1:0.8-1.2:0.01-0.15:2. The organic solvent used as the reaction solvent is dichloromethane, dioxane, dichloroethane, acetone, tert-butyl alcohol:water, benzene, ethyl acetate, tetrahydrofuran, acetonitrile, N,N-dimethyl formamide or dimethyl sulfoxide. The catalyst is CuI, CuBr (PPh$_3$)$_3$, CuSO$_4$.5H$_2$O:sodium ascorbate, CuBr or Cu (OAc)$_2$. The organic base is triethylamine, diisopropylethylamine, pyridine or piperidine.

Method for preparing N-((1-((2-methyl-4-aminopyrimidin-5-yl)methyl)-1H-1,2,3-triazol-4-yl)methyl)-2-(substituted phenoxy)acetyl ester(amine) compounds represented by general formula I-3: ring-closing reaction of the compounds of general formula II with substituted phenoxyacetoxypropyne in the presence of catalyst or catalyst and organic base at temperature of −10° C. to 80° C. and catalytic conditions for 1-24 hours. Method C:

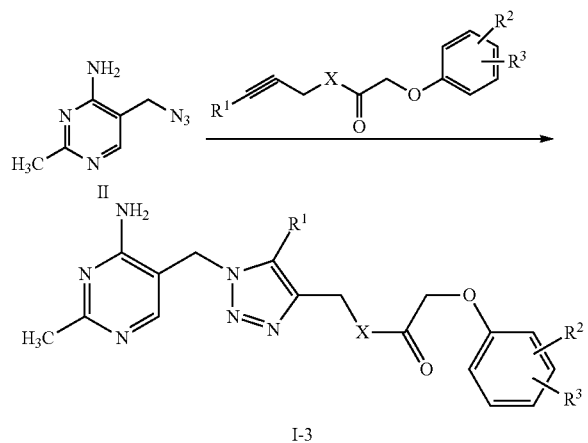

I-3 wherein X, R$^2$ and R$^3$ are defined as in general formula I-3 above.

In the reaction above, a molar ratio of the compounds of formula II to substituted phenoxyacetoxypropyne to catalyst to organic base is 1:0.8-1.2:0.01-0.15:2. The organic solvent used as the reaction solvent is dichloromethane, dioxane, dichloroethane, acetone, tert-butyl alcohol:water, benzene, ethyl acetate, tetrahydrofuran, acetonitrile, N,N-dimethyl formamide or dimethyl sulfoxide. The catalyst is CuI, CuBr (PPh$_3$)$_3$, CuSO$_4$.5H$_2$O:sodium ascorbate, CuBr or Cu (OAc)$_2$. The organic base is triethylamine, diisopropylethylamine, pyridine or piperidine.

These and other aspects of the present invention will become apparent from the following description of the preferred embodiment taken in conjunction with the following drawings, although variations and modifications therein may be effected without departing from the spirit and scope of the novel concepts of the invention.

DETAILED DESCRIPTION OF THE INVENTION

The invention is more particularly described in the following examples that are intended as illustrative only since numerous modifications and variations therein will be apparent to those skilled in the art. Various embodiments of the invention are now described in detail. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terms used in this specification generally have their ordinary meanings in the art, within the context of the invention, and in the specific context where each term is used. Certain terms that are configured to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

As used in the description herein and throughout the claims that follow, the meaning of "a", "an", and "the" includes plural reference unless the context clearly dictates otherwise.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The methods for preparation of the compounds of formula I of the present invention, including the compounds of formula I-1, I-2 and I-3, will be described specifically. The present invention is merely described rather than limited by the embodiments.

Embodiment 1

Preparation of Compound 1

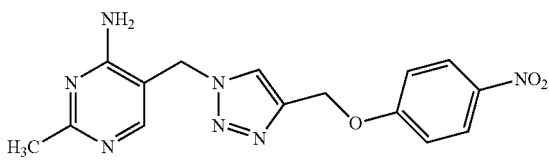 [SMILES: Cc1ncc(Cn2cc(COc3ccc([N+](=O)[O-])cc3)nn2)c(N)n1]

1 mmol 2-methyl-4-amino-5-azido methylpyrimidine and 1 mmol 4-nitrophenoxypropyne were dissolved in a solvent of 6 ml tert-butyl alcohol and water (ratio by volume of tert-butyl alcohol to water=2:1). 0.01 mmol blue vitriol and 0.1 mmol sodium ascorbate were added respectively thereto, and stirred at 60° C.-70° C. for 5-7 hours. After the reaction was completed, 50 ml water was added. With stirring, solid was precipitated out, then the solid precipitant was filtered by suction, and dried, to give the target compound as yellow solid. The yield is 79%, and melting point (mp) is 202-204° C.

Elementary analysis/%:

Calculated value: C, 52.78; H, 4.43; N, 28.73.

Measured value: C, 52.53; H, 4.33; N, 28.22.

$^1$H Nuclear Magnetic Resonance (NMR) (600 MHz, DMSO-d$_6$): δ 2.31 (s, 3H, CH$_3$); 5.31 (s, 2H, OCH$_2$); 5.46 (s, 2H, CH$_2$); 6.95 (s, 2H, NH$_2$); 7.25-7.26 (d, J=9.0 Hz, 2H, Ar—H); 8.02 (s, 1H, triazole CH); 8.21-8.22 (d, J=9.6 Hz, 2H, Ar—H); 8.27 (s, 1H, pyrimidine CH).

Mass Spectroscopy (MS) (70 eV) m/z (%): 342 (M+1)+.

The compounds 2-22 were prepared similar to the method of preparing compound 1. The structural data are identified as follows.

Compound 2

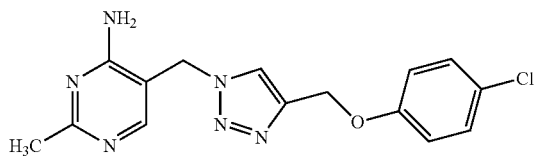 [SMILES: Cc1ncc(Cn2cc(COc3ccc(Cl)cc3)nn2)c(N)n1]

The pure product as white solid was obtained with yield of 78%, and m.p. is 168-170° C.
Elementary analysis/%:
Calculated value: C, 54.47; H, 4.57; N, 25.41.
Measured value: C, 54.74; H, 4.43; N, 25.17.
$^1$H NMR (600 MHz, DMSO-d$_6$): δ 2.31 (s, 3H, CH$_3$), 5.13 (s, 2H, OCH$_2$), 5.45 (s, 2H, CH$_2$), 6.95 (s, 2H, NH$_2$), 7.05-7.06 (d, 2H, J=9.0 Hz, Ar—H), 7.32-7.34 (d, 2H, J=9.6 Hz, Ar—H), 8.01 (s, 1H, triazole CH), 8.21 (s, 1H, pyrimidine CH).

Compound 3

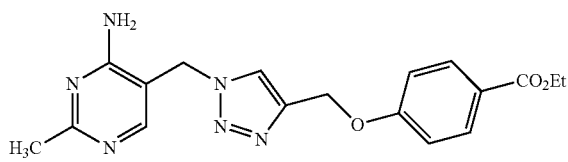

The pure product as white solid was obtained with yield of 94%, and m.p. is 190-192° C.
Elementary analysis/%:
Calculated value: C, 58.69; H, 5.47; N, 22.81.
Measured value: C, 58.88; H, 5.49; N, 22.62.
$^1$H NMR (600 MHz, DMSO-d$_6$): δ 1.28-1.31 (t, 3H, J=10.8 Hz, CH$_3$), 2.30 (s, 3H, CH$_3$), 4.24-4.29 (q, 2H, J=10.8 Hz, CH$_2$), 5.22 (s, 2H, OCH$_2$), 5.45 (s, 2H, CH$_2$), 6.93 (s, 2H, NH$_2$), 7.12-7.14 (d, 2H, J=12.6 Hz, Ar—H), 7.89-7.91 (d, 2H, J=12.6 Hz, Ar—H), 8.01 (s, 1H, triazole CH), 8.21 (s, 1H, pyrimidine CH).
ESI-MS m/z: 369 (M+1)+.

Compound 4

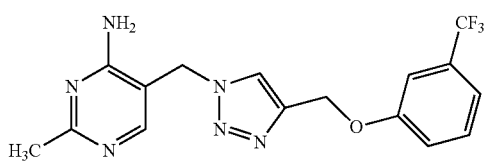 [SMILES: Cc1ncc(Cn2cc(COc3cccc(C(F)(F)F)c3)nn2)c(N)n1]

The pure product as white solid was obtained with yield of 89%, and m.p. is 160-161° C.
Elementary analysis/%:
Calculated value: C, 52.75; H, 4.15; N, 23.07.
Measured value: C, 52.46; H, 4.35; N, 22.94.

$^1$H NMR (600 MHz, DMSO-d$_6$): δ 2.31 (s, 3H, CH$_3$), 5.23 (s, 2H, OCH$_2$), 5.46 (s, 2H, CH$_2$), 6.96 (s, 2H, NH$_2$), 7.30-7.31 (d, 1H, J=7.8 Hz, Ar—H), 7.34-7.36 (t, 2H, J=8.4 Hz, 12.0 Hz, Ar—H), 7.52-7.53 (d, 1H, J=7.8 Hz, Ar—H), 8.02 (s, 1H, triazole CH), 8.24 (d, 1H, pyrimidine CH).

Compound 5

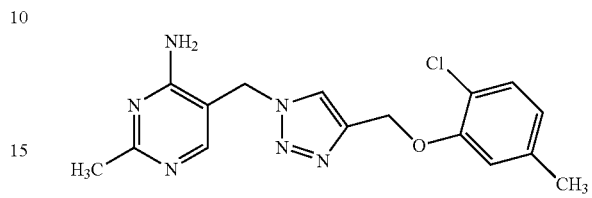

The pure product as white solid was obtained with yield of 80%, and m.p. is 184-185° C.
Elementary analysis/%:
Calculated value: C, 55.73; H, 4.97; N, 24.37.
Measured value: C, 55.41; H, 4.99; N, 24.44.
$^1$H NMR (600 MHz, DMSO-d$_6$): δ 2.30 (s, 3H, CH$_3$), 2.31 (s, 3H, CH3), 5.20-5.21 (d, 2H, J=5.4 Hz, OCH$_2$), 5.46-5.47 (d, 2H, J=6.0 Hz, CH$_2$), 6.79 (s, 1H, Ar—H), 6.96 (s, 2H, NH$_2$), 7.17-7.18 (d, 1H, J=5.4 Hz, Ar—H), 7.27-7.29 (d, 1H, J=7.2 Hz, Ar—H), 8.03 (s, 1H, triazole CH), 8.25 (s, 1H, pyrimidine CH).

Compound 6

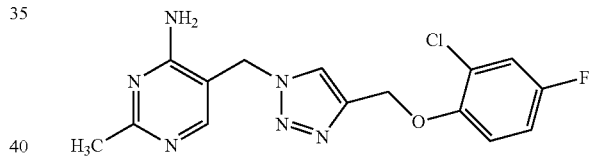

The pure product as white solid was obtained with yield of 78%, and m.p. is 169-171° C.
Elementary analysis/%:
Calculated value: C, 58.69; H, 5.47; N, 22.81.
Measure value: C, 58.88; H, 5.49; N, 22.62.
$^1$H NMR (600 MHz, DMSO-d$_6$): δ 2.31 (s, 3H, CH$_3$), 5.21 (s, 2H, OCH$_2$), 5.46 (s, 2H, CH$_2$), 6.95 (s, 2H, NH$_2$), 7.18-7.21 (dd, 1H, J=6.6 Hz, 7.8 Hz, Ar—H), 7.35-7.38 (m, 1H, Ar—H), 7.43-7.44 (d, 1H, J=6.0 Hz, Ar—H), 8.01 (s, 1H, triazole CH), 8.23 (s, 1H, pyrimidine CH).
ESI-MS m/z: 349 (M+1)+.

Compound 7

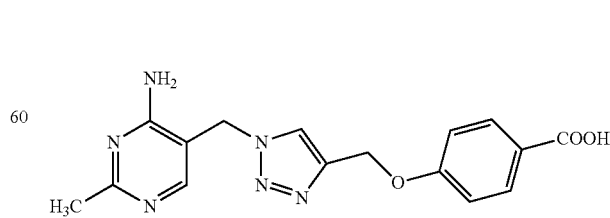

The pure product as white solid was obtained with yield of 76%, and m.p. >260° C.

Elementary analysis/%:

Calculated value: C, 56.47; H, 4.74; N, 24.69.

Measured value: C, 56.35; H, 4.74; N, 24.45.

$^1$H NMR (600 MHz, DMSO-d$_6$): δ 2.34 (s, 3H, CH$_3$), 5.22 (s, 2H, OCH$_2$), 5.47 (s, 2H, CH$_2$), 7.11-7.13 (d, 2H, J=13.2 Hz, Ar—H), 7.20 (s, 2H, NH$_2$), 7.88-7.90 (d, 2H, J=12.6 Hz, Ar—H), 8.06 (s, 1H, triazole CH), 8.26 (s, 1H, pyrimidine CH).

ESI-MS m/z: 341 (M+1)$^+$.

Compound 8

The pure product as yellow solid was obtained with yield of 50%, and m.p. is 210-211° C.

Elementary analysis/%:

Calculated value: C, 46.63; H, 3.65; N, 29.01.

Measured value: C, 46.45; H, 3.86; N, 28.81.

$^1$H NMR (600 MHz, DMSO-d$_6$): δ 2.30 (s, 3H, CH$_3$), 5.47 (s, 2H, OCH$_2$), 5.52 (s, 2H, CH$_2$), 6.98 (s, 2H, NH$_2$), 7.80-7.83 (d, 1H, J=14.4 Hz, Ar—H), 8.27 (s, 1H, pyrimidine CH), 8.51-8.54 (m, 1H, Ar—H), 8.75-8.75 (d, 1H, J=4.2 Hz, Ar—H).

$^{13}$C NMR (DMSO-d$_6$, 150 MHz): δ 25.2, 46.9, 63.6, 108.5, 116.2, 121.2, 125.3, 129.2, 138.7, 139.9, 141.0, 155.2, 155.9, 161.6, 167.3.

ESI-MS m/z: 387 (M+1)$^+$.

Compound 9

The pure product as white solid was obtained with yield of 85%, and m.p. is 142-143° C.

Elementary analysis/%:

Calculated value: C, 58.69; H, 5.47; N, 22.81.

Measured value: C, 58.77; H, 5.48; N, 22.67.

$^1$H NMR (600 MHz, DMSO-d$_6$): δ 2.30 (s, 3H, CH$_3$), 3.59 (s, 5H, CH$_2$+CH$_3$), 5.10 (s, 2H, OCH$_2$), 5.44 (s, 2H, CH$_2$), 6.95 (s, 2H, NH$_2$), 6.96-6.97 (d, 2H, J=8.4 Hz, Ar—H), 7.16-7.18 (d, 2H, J=9.0 Hz, Ar—H), 8.01 (s, 1H, triazole CH), 8.20 (d, 1H, pyrimidine CH).

$^{13}$C NMR (DMSO-d$_6$, 150 MHz): δ 25.2, 39.9, 46.7, 51.6, 61.0, 108.2, 114.4, 114.6, 124.5, 126.6, 130.9, 142.8, 156.9, 161.5, 167.0, 171.8.

ESI-MS m/z: 369 (M+1)$^+$.

Compound 10

The pure product as white solid was obtained with yield of 70%, and m.p. is 175-177° C.

Elementary analysis/%:

Calculated value: C, 58.69; H, 5.47; N, 22.81.

Measured value: C, 58.77; H, 5.48; N, 22.67.

$^1$H NMR (600 MHz, DMSO-d$_6$): δ 2.31 (s, 3H, CH$_3$), 5.24 (s, 2H, OCH$_2$), 5.46 (s, 2H, CH$_2$), 6.96 (s, 2H, NH$_2$), 7.38 (s, 2H, Ar—H), 7.57 (s, 1H, Ar—H), 8.01 (s, 1H, triazole CH), 8.25 (s, 1H, pyrimidine CH).

ESI-MS m/z: 365.22 (M+1)$^+$.

Compound 11

The pure product as yellow solid was obtained with yield of 74%, and m.p. is 142-143° C.

Elementary analysis/%:

Calculated value: C, 55.73; H, 4.97; N, 24.37.

Measured value: C, 55.63; H, 4.86; N, 24.39.

$^1$H NMR (600 MHz, DMSO-d$_6$): δ 2.28 (s, 3H, CH$_3$), 2.31 (s, 3H, CH$_3$), 5.11 (s, 2H, OCH$_2$), 5.45 (s, 2H, CH$_2$), 6.95 (s, 2H, NH$_2$), 6.89 (s, 1H, Ar—H), 7.03-7.04 (d, 2H, J=3.6 Hz, Ar—H), 7.28-7.31 (d, 2H, J=14.4 Hz, Ar—H), 8.00 (s, 1H, triazole CH), 8.20 (s, 1H, pyrimidine CH).

Compound 12

The pure product as white solid was obtained with yield of 97%, and m.p. is 132-133° C.

Elementary analysis/%:

Calculated value: C, 60.80; H, 5.44; N, 28.36.

Measured value: C, 60.62; H, 5.35; N, 28.60.

$^1$H NMR (600 MHz, CDCl$_3$): δ 2.50 (s, 3H, CH$_3$), 5.18 (s, 2H, OCH$_2$), 5.36 (s, 2H, CH$_2$), 5.59 (s, 2H, NH$_2$), 6.95-6.99 (m, 3H, Ar—H), 7.27-7.30 (t, J=7.8 Hz, Ar—H), 7.62 (s, 1H, triazole CH), 8.19 (s, 1H, pyrimidine CH).

ESI-MS m/z: 297 (M+1)$^+$.

Compound 13

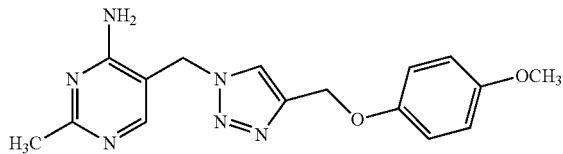

The pure product as white solid was obtained with yield of 87%, and m.p. is 115-117° C.
Elementary analysis/%:
Calculated value: C, 58.88; H, 5.56; N, 25.75.
Measured value: C, 58.97; H, 5.86; N, 25.45.
$^1$H NMR (600 MHz, CDCl$_3$): δ 2.50 (s, 3H, CH$_3$), 3.77 (s, 3H, CH$_3$), 5.13 (s, 2H, OCH$_2$), 5.36 (s, 2H, CH$_2$), 5.60 (s, 2H, NH$_2$), 6.82-6.83 (d, 2H, J=9.0 Hz, Ar—H), 6.89-6.90 (d, 2H, J=8.4 Hz, Ar—H), 7.61 (s, 1H, triazole CH), 8.19 (d, 1H, pyrimidine CH).
ESI-MS m/z: 327 (M+1)$^+$.

Compound 14

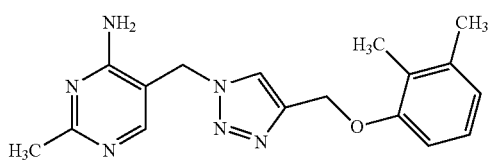 [SMILES: Cc1ncc(Cn2cc(COc3cccc(C)c3C)nn2)c(N)n1]

The pure product as white solid was obtained with yield of 50%, and m.p. is 202-204° C.
Elementary analysis/%:
Calculated value: C, 62.95; H, 6.21; N, 25.91.
Measured value: C, 62.55; H, 6.37; N, 26.00.
$^1$H NMR (600 MHz, DMSO-d$_6$): δ 2.03 (s, 3H, 2-phenyl-CH$_3$), 2.20 (s, 3H, 3-phenyl-CH$_3$), 2.31 (s, 3H, CH$_3$), 5.10 (s, 2H, OCH$_2$), 5.45 (s, 2H, CH$_2$), 6.76-6.78 (d, 1H, J=7.2 Hz, Ar—H), 6.95-6.96 (d, 2H, J=7.8 Hz, Ar—H), 7.02-7.04 (t, 1H, J=7.8 Hz, Ar—H), 7.99 (s, 1H, triazole CH), 8.21 (s, 1H, pyrimidine CH).
ESI-MS m/z: 325 (M+1)$^+$.

Compound 15

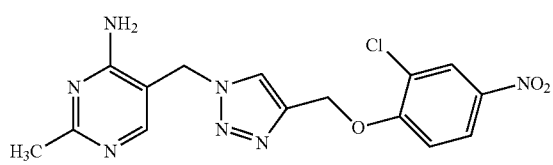 [SMILES: Cc1ncc(Cn2cc(COc3ccc([N+](=O)[O-])cc3Cl)nn2)c(N)n1]

The pure product as yellow solid was obtained with yield of 81%, and m.p. is 194-196° C.
Elementary analysis/%:
Calculated value: C, 47.94; H, 3.76; N, 26.09.
Measured value: C, 47.59; H, 3.74; N, 22.82.
$^1$H NMR (600 MHz, DMSO-d$_6$): δ 2.31 (s, 3H, CH$_3$), 5.31 (s, 2H, OCH$_2$), 5.46 (s, 2H, CH$_2$), 6.95 (s, 2H, NH$_2$), 7.25-7.26 (d, 2H, J=9.0 Hz, Ar—H), 8.02 (s, 1H, triazole CH), 8.21-8.22 (d, 2H, J=9.6 Hz, Ar—H), 8.27 (s, 1H, pyrimidine CH).
ESI-MS m/z: 376 (M+1)$^+$.

Compound 16

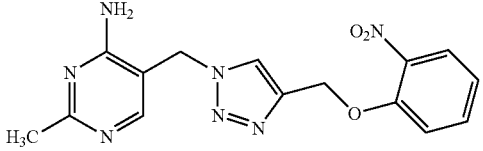

The pure product as yellow solid was obtained with yield of 90%, and m.p. is 184-185° C.
Elementary analysis/%:
Calculated value: C, 52.78; H, 4.43; N, 28.73.
Measured value: C, 52.64; H, 4.36; N, 28.31.
$^1$H NMR (600 MHz, DMSO-d$_6$): δ 2.31 (s, 3H, CH$_3$), 5.34 (s, 2H, OCH$_2$), 5.46 (s, 2H, CH$_2$), 6.95 (s, 2H, NH$_2$), 7.13-7.15 (dd, 1H, J=7.2 Hz, 7.8 Hz, Ar—H), 7.57-7.58 (d, 1H, J=8.4 Hz, Ar—H), 7.65-7.68 (d, 1H, J=7.8 Hz, Ar—H), 7.85-7.87 (d, 1H, J=7.8 Hz, Ar—H), 8.01 (s, 1H, triazole CH), 8.23 (s, 1H, pyrimidine CH).

Compound 17

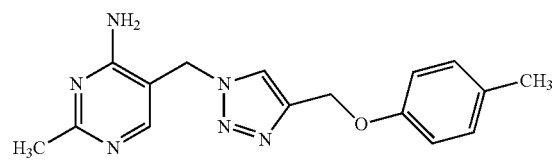

The pure product as white solid was obtained with yield of 73%, and m.p. is 157-158° C.
Elementary analysis/%:
Calculated value: C, 61.92; H, 5.85; N, 27.08.
Measured value: C, 61.74; H, 5.76; N, 27.32.
$^1$H NMR (600 MHz, CDCl$_3$): δ 2.29 (s, 3H, CH$_3$), 2.51 (s, 3H, CH$_3$), 5.16 (s, 2H, CH$_2$), 5.36 (s, 2H, CH$_2$), 5.58 (s, 2H, NH$_2$), 6.85-6.86 (d, 2H, J=8.4 Hz, Ar—H), 7.08-7.09 (d, 2H, J=8.4 Hz, Ar—H), 7.62 (s, 1H, triazole CH), 8.19 (s, 1H, pyrimidine CH).

Compound 18

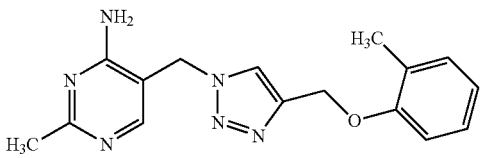 [SMILES: Cc1ncc(Cn2cc(COc3ccccc3C)nn2)c(N)n1]

The pure product as yellow solid was obtained with yield of 45%, and m.p. is 153-154° C.
Elementary analysis/%:
Calculated value: C, 61.92; H, 5.85; N, 27.08.
Measured value: C, 61.81; H, 5.91; N, 28.22.

¹H NMR (600 MHz, CDCl₃): δ 2.21 (s, 3H, CH₃), 2.51 (s, 3H, CH₃), 5.19 (s, 2H, CH₂), 5.37 (s, 2H, CH₂), 5.62 (s, 2H, NH₂), 6.88-6.92 (m, 2H, Ar—H), 7.14-7.17 (t, 2H, J=7.8, 8.4 Hz, Ar—H), 7.61 (s, 1H, triazole CH), 8.20 (s, 1H, pyrimidine CH).

Compound 19

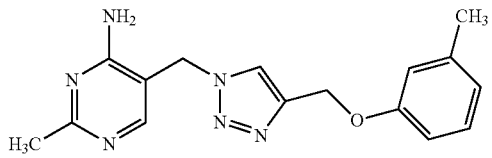 [SMILES: Cc1cccc(OCc2cn(Cc3cnc(C)nc3N)nn2)c1]

The pure product as white solid was obtained with yield of 73%, and m.p. is 58-59° C.
Elementary analysis/%:
Calculated value: C, 61.92; H, 5.85; N, 27.08.
Measured value: C, 61.77; H, 5.67; N, 26.92.
¹H NMR (600 MHz, CDCl₃): δ 2.32 (s, 3H, CH₃), 2.50 (s, 3H, CH₃), 5.17 (s, 2H, CH₂), 5.36 (s, 2H, CH₂), 5.61 (s, 2H, NH₂), 6.76-6.80 (m, 3H, ArH), 7.16-7.18 (t, 1H, J=7.8, 7.8 Hz, ArH), 7.63 (s, 1H, triazole CH), 8.19 (s, 1H, pyrimidine CH).

Compound 20

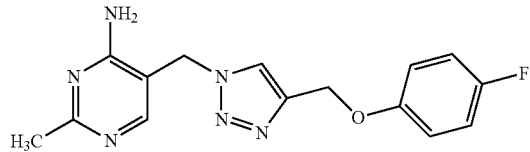 [SMILES: Cc1ncc(Cn2cc(COc3ccc(F)cc3)nn2)c(N)n1]

The pure product as white solid was obtained with yield of 63%, and m.p. is 178-179° C.
Elementary analysis/%:
Calculated value: C, 57.32; H, 4.81; N, 26.74.
Measured value: C, 57.21; H, 4.67; N, 26.55.
¹H NMR (600 MHz, CDCl₃): δ 2.50 (s, 3H, CH₃), 5.14 (s, 2H, CH₂), 5.37 (s, 2H, CH₂), 5.63 (s, 2H, NH₂), 6.89-6.91 (m, 2H, Ar—H), 6.96-6.99 (t, 2H, J=8.4, 8.4 Hz, Ar—H), 7.63 (s, 1H, triazole CH), 8.20 (s, 1H, pyrimidine CH).

Compound 21

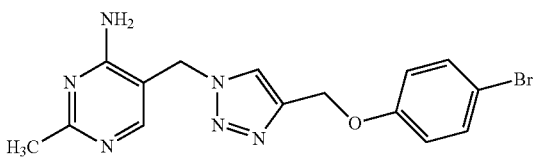 [SMILES: Cc1ncc(Cn2cc(COc3ccc(Br)cc3)nn2)c(N)n1]

The pure product as yellow solid was obtained with yield of 74%, and m.p. is 167-168° C.
Elementary analysis/%:
Calculated value: C, 48.01; H, 4.03; N, 22.40.
Measured value: C, 47.87; H, 4.32; N, 22.21.
¹H NMR (600 MHz, CDCl₃): δ 2.50 (s, 3H, CH₃), 5.15 (s, 2H, CH₂), 5.36 (s, 2H, CH₂), 5.59 (s, 2H, NH₂), 6.84-6.85 (d, 2H, J=9.0 Hz, Ar—H), 7.37-7.38 (d, 2H, J=8.4 Hz, Ar—H), 7.62 (s, 1H, triazole CH), 8.19 (s, 1H, pyrimidine CH).

Compound 22

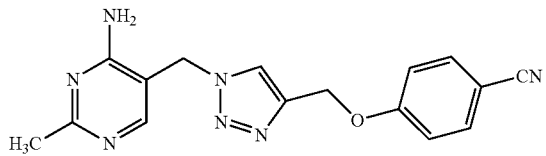 [SMILES: Cc1ncc(Cn2cc(COc3ccc(C#N)cc3)nn2)c(N)n1]

The pure product as white solid was obtained with yield of 62%, and m.p. is 185-186° C.
Elementary analysis/%:
Calculated value: C, 59.80; H, 4.71; N, 30.51.
Measured value: C, 59.77; H, 4.66; N, 30.42.
¹H NMR (600 MHz, DMSO-d₆): δ 2.31 (s, 3H, CH₃), 5.32 (s, 2H, OCH₂), 5.45 (s, 2H, CH₂), 6.95 (s, 2H, NH₂), 7.22-7.23 (d, 2H, J=8.4 Hz, Ar—H), 7.79-7.80 (d, 2H, J=8.4 Hz, Ar—H) 8.02 (s, 1H, triazole CH), 8.27 (s, 1H, pyrimidine CH).

Embodiment 2

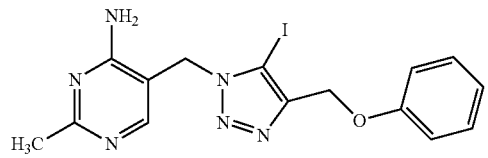 [SMILES: Cc1ncc(Cn2nnc(COc3ccccc3)c2I)c(N)n1]

Preparation of Compound 23

1 mmol 2-methyl-4-amino-5-azidomethylpyrimidine and 1 mmol iodo-4-nitrophenoxypropyne were dissolved in 5 ml anhydrous tetrahydrofuran. 0.05 mmol CuI and 2 mmol triethylamine were added respectively thereto, and stirred for 12 hours at 40-50° C. Upon addition of water at stirring, solid was precipitated out. The solid precipitant was filtered by suction, and dried to give the yellow solid, with yield of 75%, and m.p. is 127-129° C.

Elementary analysis/%:
Calculated value: C, 42.67; H, 3.58; N, 19.90.
Measured value: C, 42.89; H, 3.59; N, 19.95.
¹H NMR (600 MHz, DMSO-d₆): δ 2.32 (s, 3H, CH3), 5.06 (s, 2H, CH2), 5.45 (s, 2H, CH₂), 6.97 (s, 2H, NH₂), 7.05 (s, 3H, Ar—H), 7.31 (s, 2H, Ar—H), 7.69 (s, 1H, pyrimidine CH).
¹³C NMR (DMSO-d₆, 125 MHz): δ 25.27, 48.01, 61.37, 86.15, 107.49, 114.80, 121.16, 129.58, 147.38, 155.09, 158.16, 161.41, 166.86.
ESI-MS m/z: 423 (M+1)⁺.

The compounds 24-31 and 80-87 were prepared in analogy to the compound 23, with structural data identified as follows.

Compound 24

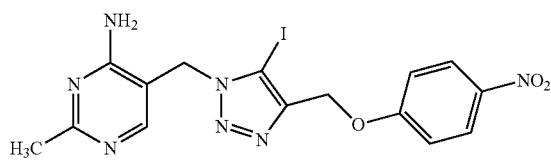 [SMILES: Cc1ncc(Cn2nnc(COc3ccc([N+](=O)[O-])cc3)c2I)c(N)n1]

The pure product as yellow solid was obtained with yield of 74%, and m.p. is 215-217° C.

Elementary analysis/%:

Calculated value: C, 38.56; H, 3.02; N, 20.99.

Measured value: C, 38.26; H, 3.00; N, 21.35.

$^1$H NMR (600 MHz, DMSO-d$_6$): δ 2.34 (s, 3H, CH$_3$), 5.26 (s, 2H, CH$_2$), 5.49 (s, 2H, CH$_2$), 6.98 (s, 2H, NH$_2$), 7.26-7.29 (d, 2H, J=7.8 Hz, Ar—H), 8.22-8.24 (d, 2H, J=9.0 Hz, Ar—H), 8.27 (s, 1H, pyrimidine CH).

ESI-MS m/z (%): 468 (M+1)$^+$.

Compound 25

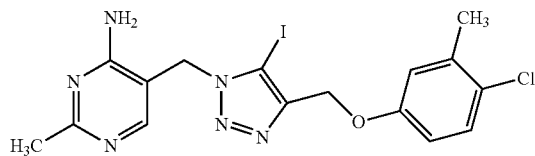 [SMILES: Cc1ncc(Cn2nnc(COc3ccc(Cl)c(C)c3)c2I)c(N)n1]

The pure product as yellow solid was obtained with yield of 74%, and m.p. is 215-217° C.

Elementary analysis/%:

Calculated value: C, 40.83; H, 3.43; N, 17.85.

Measured value: C, 40.58; H, 3.26; N, 17.49.

$^1$H NMR (600 MHz, DMSO-d$_6$): δ 2.29 (s, 3H, CH$_3$), 2.33 (s, 3H, CH$_3$), 5.05 (s, 2H, CH$_2$), 5.47 (s, 2H, CH$_2$), 6.90-6.92 (m, 3H), 7.06-7.08 (d, 1H, J=2.4 Hz, Ar—H), 7.30-7.32 (d, 1H, J=9.0 Hz, Ar—H).

Compound 26

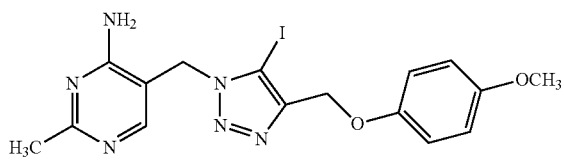 [SMILES: COc1ccc(OCc2nnn(Cc3cnc(C)nc3N)c2I)cc1]

The pure product as yellow solid was obtained with yield of 83%, and m.p. is 177-179° C.

Elementary analysis/%:

Calculated value: C, 42.49; H, 3.79; N, 18.58.

Measured value: C, 42.45; H, 3.86; N, 18.26.

$^1$H NMR (600 MHz, DMSO-d$_6$): δ 2.32 (s, 3H, CH$_3$), 3.70 (s, 3H, OCH$_3$), 4.99 (s, 2H, CH$_2$), 5.45 (s, 2H, CH$_2$), 6.85-6.88 (t, 3H, J=6.6 Hz, 8.4 Hz), 6.88-6.91 (d, 1H, J=8.4 Hz), 6.92 (s, 1H), 6.96-6.98 (d, 1H, J=9.0 Hz).

Compound 27

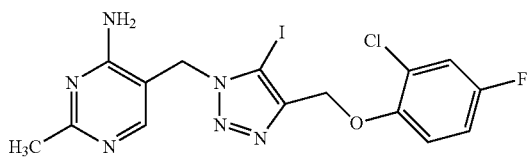 [SMILES: Cc1ncc(Cn2nnc(COc3ccc(F)cc3Cl)c2I)c(N)n1]

The pure product as yellow solid was obtained with yield of 94%, and m.p. is 187-189° C.

Elementary analysis/%:

Calculated value: C, 37.96; H, 2.76; N, 17.71.

Measured value: C, 38.00; H, 2.88; N, 17.44. $^1$H NMR (600 MHz, DMSO-d$_6$): δ 2.33 (s, 3H, CH$_3$), 5.15 (s, 2H, CH$_2$), 5.45 (s, 2H, CH$_2$), 6.90 (s, 2H, NH$_2$), 7.21 (s, 1H, Ar—H), 7.36 (s, 1H, Ar—H), 7.43-7.44 (d, 1H, J=5.4 Hz, Ar—H), 7.68 (s, 1H).

Compound 28

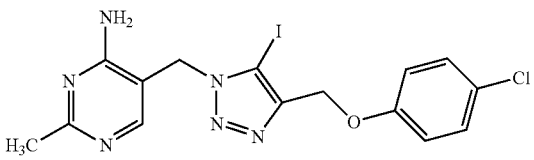 [SMILES: Cc1ncc(Cn2nnc(COc3ccc(Cl)cc3)c2I)c(N)n1]

The pure product as yellow solid was obtained with yield of 87%, and m.p. is 183-185° C.

Elementary analysis/%:

Calculated value: C, 39.45; H, 3.09; N, 18.40.

Measured value: C, 39.58; H, 3.12; N, 18.58.

$^1$H NMR (600 MHz, DMSO-d$_6$): δ 2.31 (s, 3H, CH$_3$), 5.12 (s, 2H, CH$_2$), 5.45 (s, 2H, CH$_2$), 6.94 (s, 2H, NH$_2$), 6.99-7.08 (m, 2H, Ar—H), 7.34-7.35 (d, 3H, J=9.0 Hz, Ar—H).

Compound 29

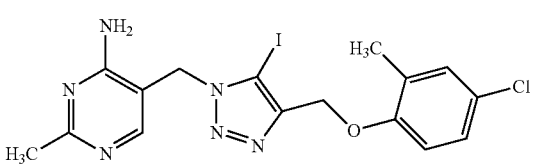 [SMILES: Cc1ncc(Cn2nnc(COc3ccc(Cl)cc3C)c2I)c(N)n1]

The pure product as yellow solid was obtained with yield of 86%, and m.p. is 163-165° C.

Elementary analysis/%:

Calculated value: C, 40.83; H, 3.43; N, 17.85.

Measured value: C, 41.18; H, 3.83; N, 17.67.

$^1$H NMR (600 MHz, CDCl$_3$): δ 2.21 (s, 3H, CH$_3$), 2.51 (s, 3H, CH$_3$), 5.08 (s, 2H, CH$_2$), 5.42 (s, 2H, CH$_2$), 5.77 (s, 2H,

NH$_2$), 6.91-6.93 (d, 1H, J=9.6 Hz, Ar—H), 7.10 (s, 2H, Ar—H), 8.42 (s, 1H, pyrimidine CH).

Compound 30

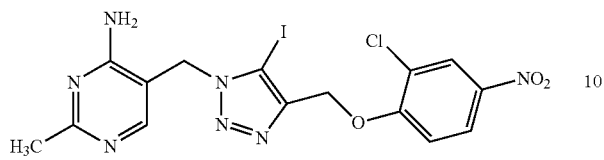

The pure product as yellow solid was obtained with yield of 85%, and m.p. is 223-225° C.
Elementary analysis/%:
Calculated value: C, 40.83; H, 3.43; N, 17.85.
Measured value: C, 41.18; H, 3.83; N, 17.67.
$^1$H NMR (600 MHz, DMSO-d$_6$): δ 2.30 (s, 3H, CH$_3$), 5.36 (s, 2H, CH$_2$), 5.45 (s, 2H, CH$_2$), 6.91 (s, 2H, NH$_2$), 7.60-7.61 (d, 1H, J=8.4 Hz, Ar—H), 8.24-8.25 (d, 1H, J=7.8 Hz, Ar—H), 8.30 (s, 1H, Ar—H).
$^{13}$C NMR (125 Mz, DMSO-d$_6$): δ 25.28, 48.09, 63.39, 86.83, 114.11, 122.14, 124.59, 125.61, 141.12, 146.23, 155.15, 158.61, 161.45.

Compound 31

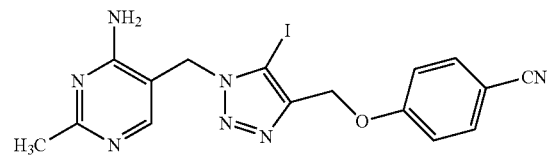 [SMILES: Cc1ncc(Cn2nnc(COc3ccc(C#N)cc3)c2I)c(N)n1]

The pure product as yellow solid was obtained with yield of 88%, and m.p. is 199-201° C.
Elementary analysis/%:
Calculated value: C, 42.97; H, 3.16; N, 21.92.
Measured value: C, 42.64; H, 3.31; N, 21.68.
$^1$H NMR (600 MHz, DMSO-d$_6$): δ 2.35 (s, 3H, CH$_3$), 5.18 (s, 2H, CH$_2$), 5.46 (s, 2H, CH$_2$), 7.06 (s, 2H, NH$_2$), 7.22-7.23 (d, 2H, J=8.4 Hz, Ar—H), 7.78-7.79 (d, 2H, J=8.4 Hz, Ar—H).
$^{13}$C NMR (125 Mz, DMSO-d$_6$): δ 25.69, 47.93, 61.88, 86.61, 103.40, 115.88, 119.11, 134.26, 124.64, 146.69, 154.57, 161.24, 161.52.

Compound 80

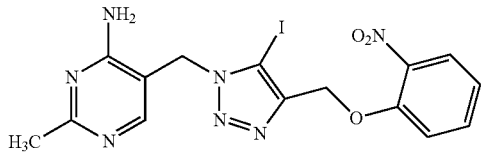

The pure product as yellow solid was obtained with yield of 86%, and m.p. is 178-180° C.
Elementary analysis/%:
Calculated value: C, 38.56; H, 3.02; N, 20.99.
Measured value: C, 38.26; H, 3.42; N, 20.67.

$^1$H NMR (400 MHz, DMSO-d$_6$): δ 2.34 (s, 3H, CH$_3$), 5.29 (s, 2H, CH$_2$), 5.46 (s, 2H, CH$_2$), 6.97 (s, 2H, NH$_2$), 7.16 (s, 1H, Ar—H), 7.60 (s, 1H, Ar—H), 7.68 (s, 1H, Ar—H), 7.85 (s, 1H, Ar—H).
E-MS (m/z, %): 467.25 (M$^+$, 0.45).

Compound 81

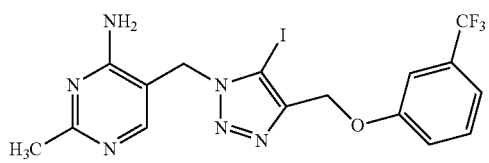 [SMILES: Cc1ncc(Cn2nnc(COc3cccc(C(F)(F)F)c3)c2I)c(N)n1]

The pure product as yellow solid was obtained with yield of 65%, and m.p. is 146-148° C.
Elementary analysis/%:
Calculated value: C, 39.20; H, 2.88; N, 17.14.
Measured value: C, 39.02; H, 2.53; N, 16.85.
$^1$H NMR (400 MHz, DMSO-d$_6$): δ 2.32 (s, 3H, CH$_3$), 5.17 (s, 2H, CH$_2$), 5.46 (s, 2H, CH$_2$), 6.93 (s, 2H, NH$_2$), 7.31-7.39 (m, 3H, Ar—H), 7.54 (t, 1H, J=8.0 Hz, Ar—H).
E-MS (m/z, %): 490.47 (M$^+$, 1.00).

Compound 82

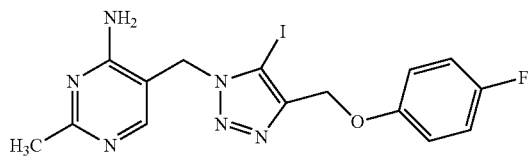 [SMILES: Cc1ncc(Cn2nnc(COc3ccc(F)cc3)c2I)c(N)n1]

The pure product as yellow solid was obtained with yield of 67%, and m.p. is 160-162° C.
Elementary analysis/%:
Calculated value: C, 40.93; H, 3.21; N, 19.09.
Measured value: C, 40.71; H, 3.15; N, 19.37.
$^1$H NMR (600 MHz, CDCl$_3$): δ 2.51 (s, 3H, CH$_3$), 5.05 (s, 2H, CH$_2$), 5.42 (s, 2H, CH$_2$), 5.76 (s, 2H, NH$_2$), 6.96-6.99 (m, 4H, Ar—H), 8.42 (s, 1H, CH).
E-MS (m/z, %): 440.94 (M$^+$+1, 2.23), 440.20 (M$^+$, 3.38).

Compound 83

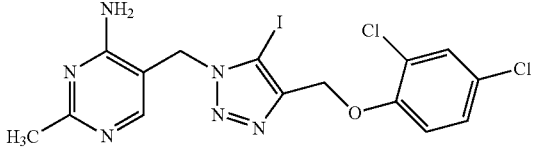 [SMILES: Cc1ncc(Cn2nnc(COc3ccc(Cl)cc3Cl)c2I)c(N)n1]

The pure product as yellow solid was obtained with yield of 84%, and m.p. is 176-177° C.
Elementary analysis/%:
Calculated value: C, 36.68; H, 2.67; N, 17.11.
Measured value: C, 36.39; H, 2.34; N, 16.96.
$^1$H NMR (400 MHz, DMSO-d$_6$): δ 2.31 (s, 3H, CH$_3$), 5.17 (s, 2H, CH$_2$), 5.45 (s, 2H, CH$_2$), 6.92 (s, 2H, NH$_2$), 7.239 (s, 2H, Ar—H), 7.57 (s, 1H, Ar—H).
E-MS (m/z, %): 491.34 (M$^+$, 0.69).

Compound 84

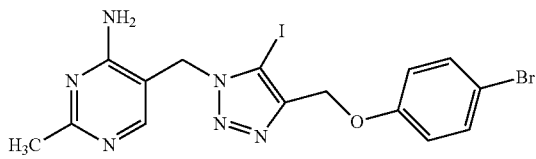 [SMILES: Cc1ncc(Cn2nnc(COc3ccc(Br)cc3)c2I)c(N)n1]

The pure product as yellow solid was obtained with yield of 75%, and m.p. is 138-140° C.

Elementary analysis/%:
Calculated value: C, 35.95; H, 2.82; N, 16.77.
Measured value: C, 35.53; H, 3.30; N, 16.80.
$^1$H NMR (400 MHz, DMSO-$d_6$): δ 2.33 (s, 3H, $CH_3$), 5.07 (s, 2H, $CH_2$), 5.47 (s, 2H, $CH_2$), 6.94 (s, 2H, $NH_2$), 7.03 (d, 2H, J=8.4 Hz, Ar—H), 7.47 (d, 2H, J=8.0 Hz, Ar—H), 8.22 (s, 1H, CH).
E-MS (m/z, %): 502.03 ($M^+$+2, 0.76), 499.91 ($M^+$, 1.17).

Compound 85

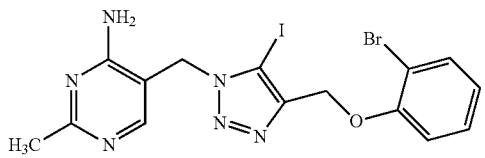 [SMILES: Cc1ncc(Cn2nnc(COc3ccccc3Br)c2I)c(N)n1]

The pure product as yellow solid was obtained with yield of 77%, and m.p. is 145-147° C.

Elementary analysis/%:
Calculated value: C, 35.95; H, 2.82; N, 16.77.
Measured value: C, 35.61; H, 3.01; N, 16.52.
$^1$H NMR (600 MHz, $CDCl_3$): δ 2.51 (s, 3H, $CH_3$), 5.18 (s, 2H, $CH_2$), 5.41 (s, 2H, $CH_2$), 5.77 (s, 2H, $NH_2$), 6.86-6.91 (m, 2H, Ar—H), 7.52-7.56 (m, 2H, Ar—H), 8.44 (s, 1H, CH).
E-MS (m/z, %): 499.95 ($M^+$, 0.65).

Compound 86

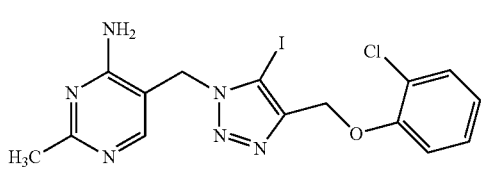 [SMILES: Cc1ncc(Cn2nnc(COc3ccccc3Cl)c2I)c(N)n1]

The pure product as yellow solid was obtained with yield of 88%, and m.p. is 168-170° C.

Elementary analysis/%:
Calculated value: C, 39.45; H, 3.09; N, 18.40.
Measured value: C, 39.46; H, 3.43; N, 18.55.
$^1$H NMR (400 MHz, DMSO-$d_6$): δ 2.32 (s, 3H, $CH_3$), 5.06 (s, 2H, $CH_2$), 5.46 (s, 2H, $CH_2$), 6.93 (s, 2H, $NH_2$), 7.08 (d, 2H, J=8.8 Hz, Ar—H), 7.34 (d, 2H, J=8.8 Hz, Ar—H).
E-MS (m/z, %): 458.27 ($M^+$+2, 0.52), 456.27 ($M^+$, 0.79).

Compound 87

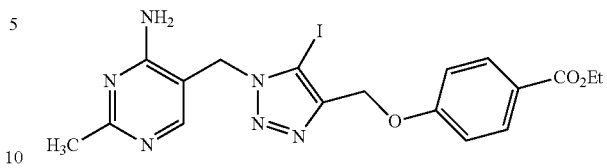

The pure product as yellow solid was obtained with yield of 80%, and m.p. is 146-147° C.

Elementary analysis/%:
Calculated value: C, 43.74; H, 3.87; N, 17.00.
Measured value: C, 43.62; H, 4.16; N, 16.72.
$^1$H NMR (400 MHz, DMSO-$d_6$): δ 1.30 (t, 3H, J=6.8 Hz, $CH_3$), 2.32 (s, 3H, $CH_3$), 4.26 (q, 2H, J=7.6 Hz, $CH_2$), 5.16 (s, 2H, $CH_2$), 5.46 (s, 2H, $CH_2$), 6.93 (s, 2H, $NH_2$), 7.16 (d, 2H, J=7.6 Hz, Ar—H), 7.92 (d, 2H, J=8.0 Hz, Ar—H).
E-MS (m/z, %): 494.04 ($M^+$, 0.91).

Embodiment 3

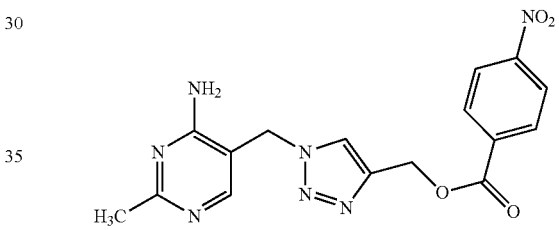

Preparation of Compound 32

1 mmol 2-methyl-4-amino-5-azidomethylpyrimidine and 1 mmol benzoyl propyne ester were dissolved in a solvent of 6 ml DMF. 0.01 mmol blue vitriol and 0.1 mmol sodium ascorbate were added respectively thereto, stirred at 0-10° C. for 5-7 hours. After the reaction was completed, 50 ml water was added. With stirring, solid precipitated out. The solid precipitant was filtered by suction, and was dried, to give the target compound as white solid, yield 88%, and m.p. is 151-153° C.

Elementary analysis/%:
Calculated value: C, 52.03; H, 4.09; N, 26.55.
Measured value: C, 52.44; H, 4.35; N, 26.13.
$^1$H NMR (600 MHz, DMSO-$d_6$): δ 2.29 (s, 3H, $CH_3$), 5.44 (s, 2H, $CH_2$), 5.45 (s, 2H, $OCH_2$), 6.96 (s, 2H, $NH_2$), 8.02 ((s, 1H, triazole CH), 8.16-8.17 (dd, 2H, J=2.4 Hz, J=6.6 Hz, Ar—H), 8.28 (s, 1H, pyrimidine CH), 8.33-8.34 (dd, 2H, J=1.2 Hz, J=7.2 Hz, Ar—H).
$^{13}$C NMR (100 MHz, DMSO-$d_6$) δ(ppm): 25.3, 47.0, 58.2, 108.6, 125.5, 127.5, 129.0, 132.0, 138.5, 141.4, 156.8, 160.9, 164.0, 167.6.

The compounds 33-42 are prepared in analogy to the compound 32, with structural data identified as follows.

Compound 33

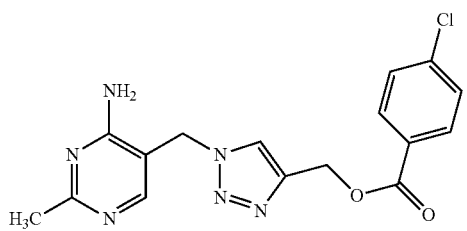 [SMILES: Cc1ncc(Cn2cc(COC(=O)c3ccc(Cl)cc3)nn2)c(N)n1]

The pure product as white solid was obtained with yield of 54%, and m.p. is 188-189° C.
Elementary analysis/%:
Calculated value: C, 53.56; H, 4.21; N, 23.42.
Measured value: C, 53.93; H, 4.15; N, 22.98.
$^1$H NMR (600 MHz, DMSO-d$_6$): δ 2.29 (s, 3H, CH$_3$), 5.37 (s, 2H, CH$_2$), 5.44 (s, 2H, OCH$_2$), 6.96 (s, 2H, NH$_2$), 7.59-7.60 (d, 2H, J=7.2 Hz, Ar—H), 7.94-7.95 (d, 2H, J=7.2 Hz, Ar—H), 8.02 ((s, 1H, triazole CH), 8.25 (s, 1H, pyrimidine CH).

Compound 34

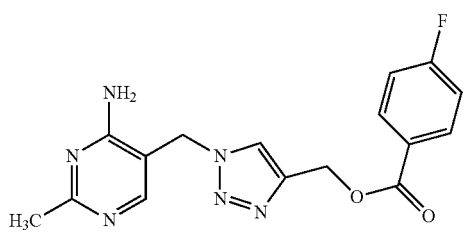

The pure product as white solid was obtained with yield of 88%, and m.p. is 198-199° C.
Elementary analysis/%:
Calculated value: C, 56.14; H, 4.42; N, 24.55.
Measured value: C, 56.44; H, 4.42; N, 24.73.
$^1$H NMR (600 MHz, DMSO-d$_6$): δ 2.29 (s, 3H, CH$_3$), 5.34 (s, 2H, CH$_2$), 5.44 (s, 2H, OCH$_2$), 6.95 (s, 2H, NH$_2$), 7.34 (s, 2H, Ar—H), 8.01 (s, 2H, Ar—H), 8.01 (s, 1H, triazole CH), 8.28 (s, 1H, pyrimidine CH).

Compound 35

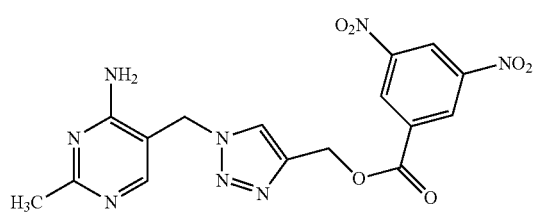 [SMILES: Cc1ncc(Cn2cc(COC(=O)c3cc([N+](=O)[O-])cc([N+](=O)[O-])c3)nn2)c(N)n1]

The pure product as white solid was obtained with yield of 75%, and m.p. is 142-143° C.
Elementary analysis/%:
Calculated value: C, 46.38; H, 3.41; N, 27.04.
Measured value: C, 46.33; H, 2.92; N, 27.14.
$^1$H NMR (600 MHz, DMSO-d$_6$): δ 2.29 (s, 3H, CH$_3$), 5.46 (s, 2H, CH$_2$), 5.51 (s, 2H, OCH$_2$), 6.96 (s, 2H, NH$_2$), 8.02 ((s, 1H, triazole CH), 8.28 (s, 1H, pyrimidine CH), 8.87 (s, 2H, Ar—H), 9.03 (s, 1H, Ar—H).

Compound 36

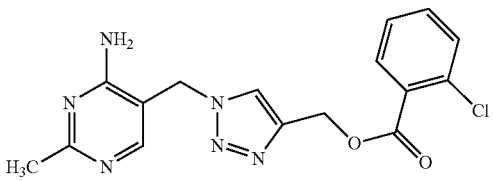

The pure product as white solid was obtained with yield of 82%, and m.p. is 85-87° C.
Elementary analysis/%:
Calculated value: C, 53.56; H, 4.21; N, 23.42.
Measured value: C, 53.17; H, 4.78; N, 23.43.
$^1$H NMR (600 MHz, DMSO-d$_6$): δ 2.29 (s, 3H, CH$_3$), 5.38 (s, 2H, CH$_2$), 5.45 (s, 2H, OCH$_2$), 6.95 (s, 2H, NH$_2$), 7.45 (s, 1H, Ar—H), 7.58 (s, 2H, Ar—H), 7.76-7.77 (d, 1H, J=5.4 Hz, Ar—H), 8.00 (s, 1H, triazole CH), 8.28 (s, 1H, pyrimidine CH).

Compound 37

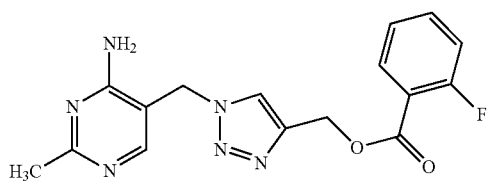 [SMILES: Cc1ncc(Cn2cc(COC(=O)c3ccccc3F)nn2)c(N)n1]

The pure product as white solid was obtained with yield of 90%, and m.p. is 124-125° C.
Elementary analysis/%:
Calculated value: C, 56.14; H, 4.42; N, 24.55.
Measured value: C, 56.26; H, 4.02; N, 24.12.
$^1$H NMR (600 MHz, DMSO-d$_6$): δ 2.31 (s, 3H, CH$_3$), 5.39 (s, 2H, CH$_2$), 5.46 (s, 2H, OCH$_2$), 6.96 (s, 2H, NH$_2$), 7.34-7.35 (d, 2H, J=7.8 Hz, Ar—H), 7.69 (s, 1H, Ar—H), 7.87-7.88 (d, 1H, J=6.6 Hz, Ar—H), 8.03 (s, 1H, triazole CH), 8.26 (s, 1H, pyrimidine CH).

Compound 38

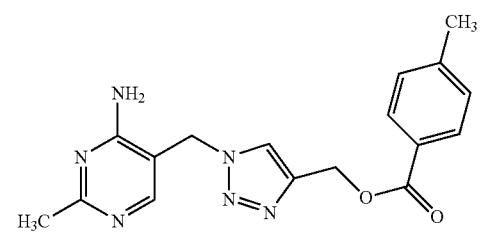

The pure product as white solid was obtained with yield of 77%, and m.p. is 202-203° C.

Elementary analysis/%:
Calculated value: C, 60.34; H, 5.36; N, 24.84.
Measured value: C, 60.42; H, 5.38; N, 24.73.
$^1$H NMR (600 MHz, DMSO-$d_6$): δ 2.29 (s, 3H, CH$_3$), 2.36 (s, 3H, CH$_3$), 5.35 (s, 2H, CH$_2$), 5.44 (s, 2H, OCH$_2$), 6.95 (s, 2H, NH$_2$), 7.31-7.33 (d, 2H, J=8.4 Hz, Ar—H), 7.82-7.84 (d, 2H, J=7.8 Hz, Ar—H), 8.01 ((s, 1H, triazole CH), 8.24 (s, 1H, pyrimidine CH).

Compound 39

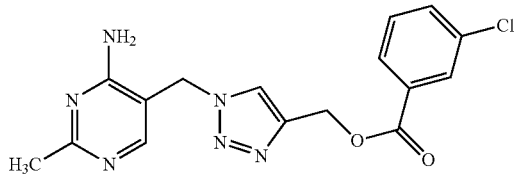 [SMILES: Cc1ncc(Cn2cc(COC(=O)c3cccc(Cl)c3)nn2)c(N)n1]

The pure product as white solid was obtained with yield of 83%, and m.p. is 165-166° C.
Elementary analysis/%:
Calculated value: C, 53.56; H, 4.21; N, 23.42.
Measured value: C, 53.04; H, 4.19; N, 23.49.
$^1$H NMR (600 MHz, DMSO-$d_6$): δ 2.29 (s, 3H, CH$_3$), 5.44 (s, 2H, OCH$_2$), 5.45 (s, 2H, CH$_2$), 6.96 (s, 2H, NH$_2$), 8.02 (s, 1H, triazole CH), 8.16-8.17 (t, 2H, J=2.4 Hz, J=6.6 Hz, Ar—H), 8.28 (s, 1H, pyrimidine CH), 8.33-8.34 (t, 2H, J=1.2 Hz, J=7.2 Hz, Ar—H).

Compound 40

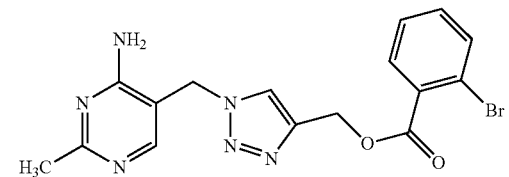 [SMILES: Cc1ncc(Cn2cc(COC(=O)c3ccccc3Br)nn2)c(N)n1]

The pure product as green solid was obtained with yield of 60%, and m.p. is 174-176° C.
Elementary analysis/%:
Calculated value: C, 53.56; H, 4.21; N, 23.42.
Measured value: C, 53.04; H, 4.19; N, 23.49.
$^1$H NMR (400 MHz, DMSO-$d_6$): δ 2.31 (s, 3H, CH$_3$), 5.39 (s, 2H, OCH$_2$), 5.47 (s, 2H, CH$_2$), 6.95 (s, 2H, NH$_2$), 7.48 (s, 2H, Ar—H), 7.73 (s, 2H, Ar—H), 8.25 (s, 1H).

Compound 41

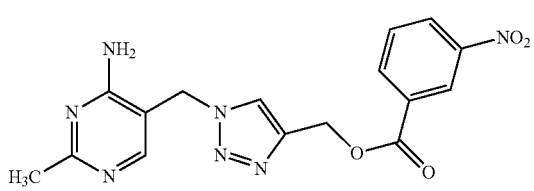

The pure product as green solid was obtained with yield of 69%, and m.p. is 159-160° C.

Elementary analysis/%:
Calculated value: C, 53.56; H, 4.21; N, 23.42.
Measured value: C, 53.04; H, 4.19; N, 23.49.
$^1$H NMR (600 MHz, DMSO-$d_6$): δ 2.29 (s, 3H, CH$_3$), 5.45 (s, 2H, OCH$_2$), 5.48 (s, 2H, CH$_2$), 6.96 (s, 2H, NH$_2$), 7.99 (s, 1H), 8.16-8.17 (m, 3H, Ar—H), 8.28 (s, 1H, pyrimidine CH).

Compound 42

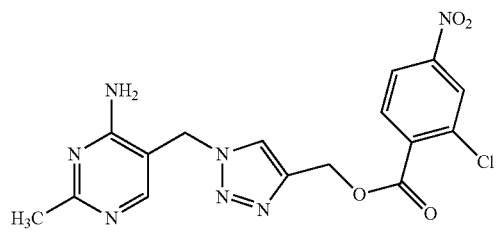 [SMILES: Cc1ncc(Cn2cc(COC(=O)c3ccc([N+](=O)[O-])cc3Cl)nn2)c(N)n1]

The pure product as green solid was obtained with yield of 59%, and m.p. is 129-130° C.
Elementary analysis/%:
Calculated value: C, 53.56; H, 4.21; N, 23.42.
Measured value: C, 53.04; H, 4.19; N, 23.49.
$^1$H NMR (400 MHz, DMSO-$d_6$): δ 2.32 (s, 3H, CH$_3$), 5.45 (s, 2H, OCH$_2$), 5.49 (s, 2H, CH$_2$), 6.95 (s, 2H, NH$_2$), 7.99-8.02 (d, 1H, J=12.6 Hz), 8.25-8.26 (d, 2H, J=5.4 Hz), 8.41 (s, 1H, pyrimidine CH).

Embodiment 4

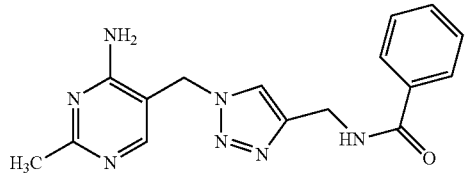

Preparation of Compound 43

1 mmol 2-methyl-4-amino-5-azidomethylpyrimidine and 1 mmol iodo-4-nitrophenoxypropyne were dissolved in 5 ml anhydrous tetrahydrofuran. 0.05 mmol CuBr and 2 mmol triethylamine were added respectively thereto, and stirred for 12 hours at 50-60° C. Upon addition of water at stirring, the solid precipitated out. The solid precipitant was filtered by suction, and dried to give the green solid, with yield of 78%, and m.p. is 197-199° C.
Elementary analysis/%:
Calculated value: C, 59.43; H, 4.95; N, 30.32.
Measured value: C, 59.19; H, 5.25; N, 30.75.
$^1$H NMR (600 MHz, DMSO-$d_6$): δ 2.28 (s, 3H, CH$_3$), 4.47-4.48 (d, 2H, J=5.4, CH$_2$), 5.38 (s, 2H, CH$_2$), 6.89 (s, 2H, NH$_2$), 7.43-7.46 (dd, 2H, J=7.8, 7.2 Hz, Ar—H), 7.50-7.51 (d, 1H, J=7.8 Hz, Ar—H), 7.84-7.85 (d, 2H, J=7.2 Hz, Ar—H), 7.98 (s, 2H, CH), 9.00 (s, 1H, NH).
IR(KBr) υ (cm$^{-1}$): 3440 (—NH$^2$), 2960 (—CH$^3$), 2920 (—CH$^2$), 1640 (—C=O), 1500 (—Ar).
The compounds 44-53 are prepared in analogy to the compound 43, with structural data identified as follows.

Compound 44

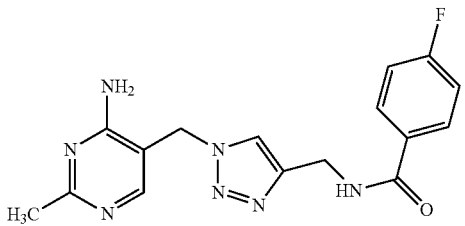

The pure product as greenish solid was obtained with yield of 65%, and m.p. is 211-212° C.
Elementary Analysis/%:
Calculated value: C, 56.30; H, 4.72; N, 28.72.
Measured value: C, 56.63; H, 4.615; N, 28.9.
$^1$H NMR (600 MHz, DMSO-$d_6$): δ 2.29 (s, 3H, CH$_3$), 4.47-4.48 (d, 2H, J=6.0, CH$_2$), 5.41 (s, 2H, CH$_2$), 6.95 (s, 2H, NH$_2$), 7.26-7.29 (m, 2H, J=6.0, 6.6, 7.2 Hz, Ar—H), 7.52-7.53 (d, 1H, J=7.2 Hz, Ar—H), 7.60-7.62 (t, 1H, J=6.0, 7.2 Hz, Ar—H), 7.99 (s, 2H, CH), 8.84 (s, 1H, NH).
IR(KBr) υ (cm$^{-1}$): 3440 (—NH$_2$), 2960 (—CH$_3$), 2920 (—CH$_2$), 1650 (—C=O), 1505 (—Ar).

Compound 45

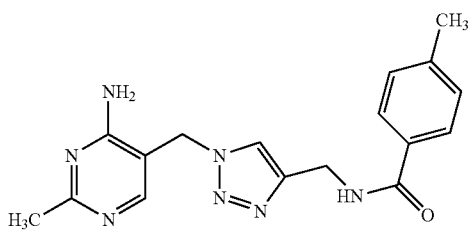

The pure product as white solid was obtained with yield of 71%, and m.p. is 132-133° C.
Elementary Analysis/%:
Calculated value: C, 60.52; H, 5.68; N, 29.06.
Measured value: C, 60.49; H, 5.805; N, 29.51.
$^1$H NMR (600 MHz, DMSO-$d_6$): δ 2.27 (s, 3H, CH$_3$), 2.32 (s, 3H, CH$_3$), 4.45 (s, 2H, CH$_2$), 5.36 (s, 2H, CH$_2$), 6.90 (s, 2H, NH$_2$), 7.24 (s, 2H, Ar—H), 7.74-7.75 (d, 2H, J=5.4 Hz, Ar—H), 7.96 (s, 2H, CH), 8.93 (s, 1H, NH).
$^{13}$C NMR (100 MHz, DMSO-$d_6$) δ(ppm): 25.5, 35.4, 47.9, 83.4, 108.5, 127.2, 128.3, 130.5, 133.7, 148.8, 154.5, 160.3, 164.5, 166.6.

Compound 46

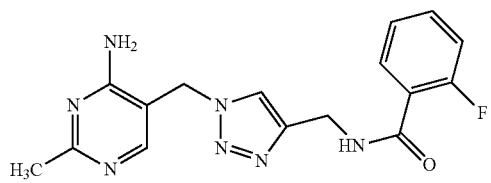 [SMILES: Cc1ncc(Cn2cc(CNC(=O)c3ccccc3F)nn2)c(N)n1]

The pure product as greenish solid was obtained with yield of 60%, and m.p. is 205-206° C.
Elementary Analysis/%:
Calculated value: C, 56.30; H, 4.72; N, 28.72.
Measured value: C, 56.79; H, 4.942; N, 28.37.
$^1$H NMR (600 MHz, DMSO-$d_6$): δ 2.31 (s, 3H, CH$_3$), 4.48-4.49 (d, 2H, J=6.0 Hz, CH$_2$), 5.43 (s, 2H, CH$_2$), 6.96 (s, 2H, NH$_2$), 7.28-7.31 (t, 2H, J=7.2 Hz, Ar—H), 7.53-7.56 (m, 1H, J=6.0, 6.0, 7.2 Hz, Ar—H), 7.62-7.64 (m, 1H, J=6.0, 6.6, 7.2, 7.8 Hz, Ar—H), 8.01 (s, 2H, CH), 8.85-8.86 (d, 1H, J=4.8 Hz, NH).
IR(KBr) υ (cm$^{-1}$): 3440 (—NH$_2$), 2960 (—CH$_3$), 2920 (—CH$_2$), 1650 (—C=O), 1505 (—Ar), 1005 (—C—F).

Compound 47

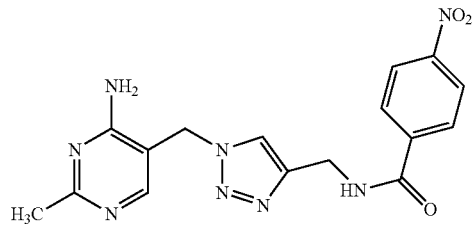 [SMILES: Cc1ncc(Cn2cc(CNC(=O)c3ccc([N+](=O)[O-])cc3)nn2)c(N)n1]

The pure product as greenish solid was obtained with yield of 93%, and m.p. is 239-240° C.
Elementary Analysis/%:
Calculated value: C, 52.17; H, 4.38; N, 30.42.
Measured value: C, 52.60; H, 4.68; N, 30.35.
$^1$H NMR (600 MHz, DMSO-$d_6$): δ 2.27 (s, 3H, CH$_3$), 4.49-4.50 (d, 2H, J=5.4 Hz, CH$_2$), 5.38 (s, 2H, CH$_2$), 6.88 (s, 2H, NH$_2$), 8.00 (s, 2H, CH), 8.05-8.07 (d, 2H, J=8.4 Hz, Ar—H), 8.28-8.29 (d, 2H, J=9.0 Hz, Ar—H), 9.32 (s, 1H, NH).
MS (EI) m/z (%): 369 (M$^+$, 18).

Compound 48

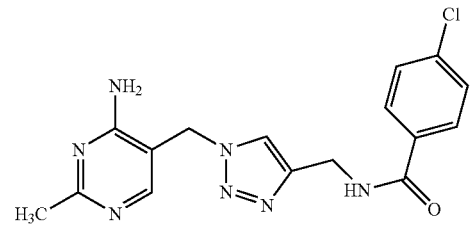

The pure product as white solid was obtained with yield of 84%, and m.p. is 165-167° C.
Elementary Analysis/%:
Calculated value: C, 53.71; H, 4.51; N, 27.40.
Measured value: C, 53.37; H, 4.778; N, 27.32.
$^1$H NMR (600 MHz, DMSO-$d_6$): δ 2.31 (s, 3H, CH$_3$), 4.50-4.51 (d, 2H, J=5.4 Hz, CH$_2$), 5.41 (s, 2H, CH$_2$), 6.92 (s, 2H, NH$_2$), 7.54-7.56 (d, 2H, J=8.4 Hz, Ar—H), 7.88-7.90 (d, 2H, J=8.4 Hz, Ar—H), 8.02 (s, 2H, CH), 9.11 (s, 1H, NH).
MS (EI) m/z (%): 357 (M$^+$, 12).

Compound 49

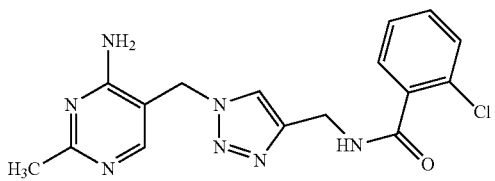 [SMILES: Cc1ncc(Cn2cc(CNC(=O)c3ccccc3Cl)nn2)c(N)n1]

The pure product as white solid was obtained with yield of 77%, and m.p. is 217-218° C.
Elementary Analysis/%:
Calculated value: C, 53.71; H, 4.51; N, 27.40.
Measured value: C, 53.51; H, 4.851; N, 27.86.
$^1$H NMR (600 MHz, DMSO-d$_6$): δ 2.27 (s, 3H, CH$_3$), 4.43-4.44 (d, 2H, J=5.4 Hz, CH$_2$), 5.41 (s, 2H, CH$_2$), 6.91 (s, 2H, NH$_2$), 7.35-7.36 (d, 1H, J=7.2 Hz, ArH), 7.38-7.39 (d, 1H, J=7.8 Hz, ArH), 7.41-7.42 (d, 1H, J=6.6 Hz, ArH), 7.45-7.46 (d, 1H, J=7.8 Hz, ArH), 7.96 (s, 2H, CH), 8.92 (s, 1H, NH).
$^{13}$C NMR (100 MHz, DMSO-d$_6$) δ(ppm): 25.8, 34.5, 47.5, 83.1, 107.8, 127.0, 127.9, 130.7, 132.1, 132.8, 147.0, 153.1, 159.8, 163.2, 164.8, 166.7, 168.5.

Compound 50

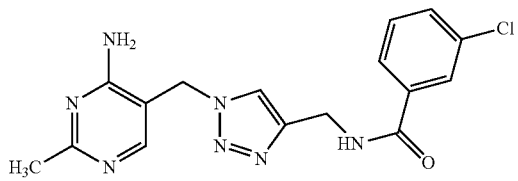

The pure product as greenish solid was obtained with yield of 99%, and m.p. is 213-214° C.
Elementary Analysis/%:
Calculated value: C, 53.71; H, 4.51; N, 27.40.
Measured value: C, 53.27; H, 4.777; N, 27.51.
$^1$H NMR (600 MHz, DMSO-d$_6$): δ 2.29 (s, 3H, CH$_3$), 4.48-4.49 (d, 2H, J=5.4 Hz, CH$_2$), 5.39 (s, 2H, CH$_2$), 6.89 (s, 2H, NH$_2$), 7.48-7.51 (d, 1H, J=8.4, 7.8 Hz, Ar—H), 7.59-7.61 (d, 1H, J=8.4 Hz, Ar—H), 7.81-7.82 (d, 1H, J=7.8 Hz, Ar—H), 7.89 (s, 1H, A-H), 8.00 (s, 2H, CH), 9.13-9.15 (t, 1H, J=5.4, 5.4 Hz, NH).
$^{13}$C NMR (100 MHz, DMSO-d$_6$) δ(ppm): 25.1, 36.1, 47.6, 82.4, 108.7, 126.9, 128.7, 139.1, 131.4, 132.9, 133.7, 148.4, 155.2, 161.1, 165.2, 167.2.

Compound 51

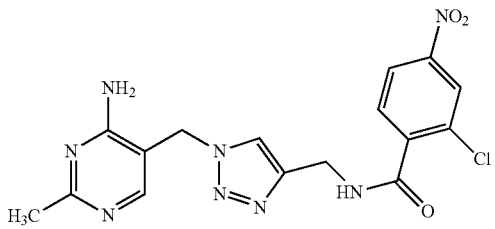 [SMILES: Cc1ncc(Cn2cc(CNC(=O)c3ccc([N+](=O)[O-])cc3Cl)nn2)c(N)n1]

The pure product as greenish solid was obtained with yield of 85%, and m.p. is >260° C.
Elementary Analysis/%:
Calculated value: C, 47.71; H, 3.75; N, 27.82.
Measured value: C, 47.61; H, 4.118; N, 27.79.
$^1$H NMR (600 MHz, DMSO-d$_6$): δ 2.29 (s, 3H, CH$_3$), 4.48-4.49 (d, 2H, J=4.8 Hz, CH$_2$), 5.43 (s, 2H, CH$_2$), 6.92 (s, 2H, NH$_2$), 7.67-7.68 (d, 1H, J=8.4, Ar—H), 8.01 (s, 2H, CH), 8.21-8.22 (d, 1H, J=7.8 Hz, Ar—H), 8.32 (s, 1H, Ar—H), 9.20 (s, 1H, NH).
IR(KBr) υ (cm$^{-1}$): 3440 (—NH$_2$), 2960 (—CH$_3$), 2920 (CH$_2$), 1640 (—C=O), 1505 (—Ar), 1355 (—NO$_2$).

Compound 52

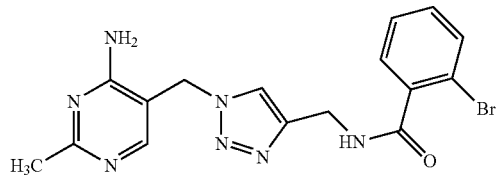

The pure product as yellow solid was obtained with yield of 54%, and m.p. is 233-234° C.
Elementary Analysis/%:
Calculated value: C, 47.77; H, 4.01; N, 24.37.
Measured value: C, 47.78; H, 4.502; N, 24.64.
$^1$H NMR (600 MHz, DMSO-d$_6$): δ 2.30 (s, 3H, CH$_3$), 4.45-4.46 (d, 2H, J=5.4 Hz, CH$_2$), 5.44 (s, 2H, CH$_2$), 6.94 (s, 2H, NH$_2$), 7.35 (s, 1H, Ar—H), 7.37-7.38 (d, 1H, J=8.4 Hz, Ar—H), 7.41-7.42 (d, 1H, J=7.2 Hz, Ar—H), 7.63-7.64 (d, 1H, J=8.4 Hz, Ar—H), 7.99 (s, 2H, CH), 8.94 (s, 1H, NH).
IR(KBr) υ (cm$^{-1}$): 3440 (—NH$_2$), 2960 (—CH$_3$), 2920 (—CH$_2$), 1640 (—C=O), 1505 (—Ar).

Compound 53

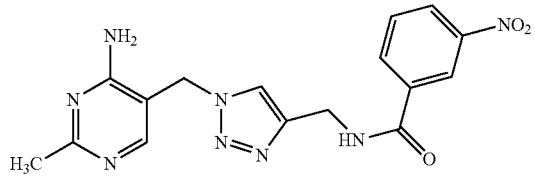 [SMILES: Cc1ncc(Cn2cc(CNC(=O)c3cccc([N+](=O)[O-])c3)nn2)c(N)n1]

The pure product as white solid was obtained with yield of 63%, and m.p. is 188-189° C.
Elementary Analysis/%:
Calculated value: C, 52.71; H, 4.51; N, 30.42.
Measured value: C, 52.88; H, 4.917; N, 30.54.
$^1$H NMR (600 MHz, DMSO-d$_6$): δ 2.28 (s, 3H, CH$_3$), 4.53 (s, 2H, CH$_2$), 5.39 (s, 2H, CH$_2$), 6.94 (s, 2H, NH$_2$), 7.78 (s, 1H, CH), 7.99 (s, 1H, Ar—H), 8.04 (s, 1H, Ar—H), 8.31 (s, 1H, Ar—H), 8.38 (s, 1H, Ar—H), 8.70 (s, 1H, CH), 9.45 (s, 1H, NH).

$^{13}$C NMR (100 MHz, DMSO-d$_6$) δ(ppm): 25.4, 35.4, 46.6, 83.1, 108.3, 127.1, 127.4, 128.8, 130.4, 133.2, 148.2, 151.7, 154.5, 160.9, 165.7, 167.6.

Additional Embodiment 4

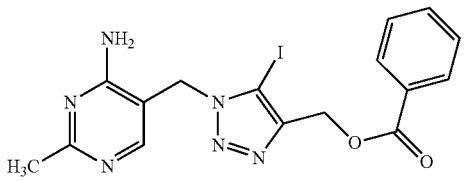

Preparation of Compound 88

1 mmol 2-methyl-4-amino-5-azidomethylpyrimidine and 1 mmol iodo-4-nitrophenoxypropyne were dissolved in 5 ml anhydrous acetonitrile. 0.05 mmol CuI and 2 mmol triethylamine were added respectively thereto, and stirred for 12 hours at 40-50° C. Upon addition of water at stirring, the solid precipitated out. The solid precipitant was filtered by suction, and dried to give the yellow solid, with yield of 91%, and m.p. is 198-199° C.

Elementary Analysis/%:

Calculated value: C, 42.68; H, 3.36; N, 18.61.

Measured value: C, 42.64; H, 3.43; N, 19.67.

$^1$H NMR (400 MHz, DMSO-d$_6$): δ 2.00 (s, 3H, CH$_3$), 4.03 (s, 2H, CH$_2$), 4.94 (s, 2H, CH$_2$), 6.43 (s, 2H, NH$_2$), 7.58-7.62 (m, 3H, Ar—H), 7.81 (s, 2H, Ar—H), 8.29 (s, 1H, pyrimidine CH).

IR(KBr) υ (cm$^{-1}$): 3426 (—NH$_2$), 2960 (—CH$_3$), 2920 (—CH$_2$), 1722 (—C=O), 1505 (—Ar).

The compounds 89-109 are prepared in analogy to the compound 88, with structural data identified as follows.

Compound 89

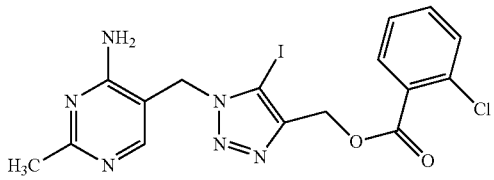 [SMILES: Cc1ncc(Cn2nnc(COC(=O)c3ccccc3Cl)c2I)c(N)n1]

The pure product as yellow solid was obtained with yield of 86%, and m.p. is 185-187° C.

Elementary Analysis/%:

Calculated value: C, 39.65; H, 2.91; N, 17.34.

Measured value: C, 39.28; H, 3.16; N, 17.79.

$^1$H NMR (400 MHz, DMSO-d$_6$): δ 2.36 (s, 3H, CH$_3$), 4.94 (s, 2H, CH$_2$), 5.50 (s, 2H, CH$_2$), 7.00 (s, 2H, NH$_2$), 7.55-7.59 (m, 2H, Ar—H), 7.76 (d, 2H, J=4.0 Hz, Ar—H), 8.18 (s, 1H, pyrimidine CH).

IR(KBr) υ (cm$^{-1}$): 3414 (—NH$_2$), 2962 (—CH$_3$), 2925 (—CH$_2$), 1737 (—C=O), 1500 (—Ar).

Compound 90

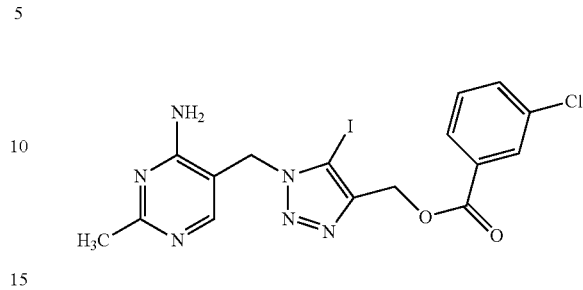

The pure product as yellow solid was obtained with yield of 86%, and m.p. is 185-187° C.

Elementary Analysis/%:

Calculated value: C, 39.65; H, 2.91; N, 17.34.

Measured value: C, 39.74; H, 2.86; N, 17.15.

$^1$H NMR (400 MHz, DMSO-d$_6$): δ 2.50 (s, 3H, CH$_3$), 4.94 (s, 2H, CH$_2$), 5.51 (s, 2H, CH$_2$), 6.93 (s, 2H, NH$_2$), 7.57 (d, 2H, J=2.4 Hz, Ar—H), 7.70 (d, 2H, J=2.4 Hz, Ar—H), 8.28 (s, 1H, pyrimidine CH).

IR(KBr) υ (cm$^{-1}$): 3473 (—NH$_2$), 2962 (—CH$_3$), 2920 (—CH$_2$), 1731 (—C=O), 1500 (—Ar).

Compound 91

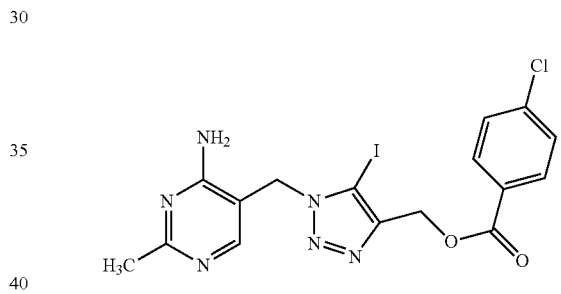

The pure product as yellow solid was obtained with yield of 84%, and m.p. is 192-193° C.

Elementary Analysis/%:

Calculated value: C, 39.65; H, 2.91; N, 17.34.

Measured value: C, 39.38; H, 2.73; N, 17.23.

$^1$H NMR (400 MHz, DMSO-d$_6$): δ 2.32 (s, 3H, CH$_3$), 5.37 (s, 2H, CH$_2$), 5.48 (s, 2H, CH$_2$), 6.94 (s, 2H, NH$_2$), 7.59 (d, 2H, J=4.0 Hz, Ar—H), 7.94 (d, 2H, J=4.0 Hz, Ar—H), 8.25 (s, 1H, pyrimidine CH).

IR(KBr) υ (cm$^{-1}$): 3409 (—NH$_2$), 3000 (—CH$_3$), 2920 (—CH$_2$), 1720 (—C=O), 1505 (—Ar).

Compound 92

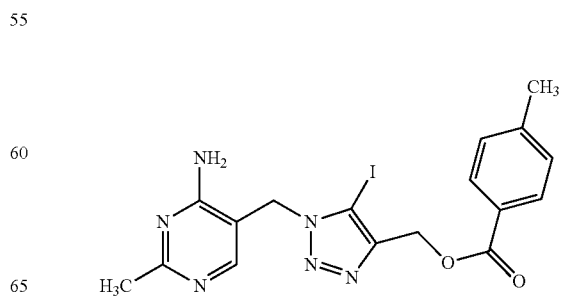

The pure product as yellow solid was obtained with yield of 75%, and m.p. is 200-201° C.

Elementary Analysis/%:

Calculated value: C, 42.51; H, 3.57; N, 17.50.

Measured value: C, 42.44; H, 3.58; N, 17.67.

$^1$H NMR (400 MHz, DMSO-d$_6$): δ 2.08 (s, 3H, CH$_3$), 2.50 (s, 3H, CH$_3$), 5.35 (s, 2H, CH$_2$), 5.51 (s, 2H, CH$_2$), 7.05 (s, 2H, NH$_2$), 7.32 (d, 2H, J=8.0 Hz, Ar—H), 7.83 (d, 2H, J=8.0 Hz, Ar—H), 8.24 (s, 1H, pyrimidine CH).

IR(KBr) υ (cm$^{-1}$): 3428 (—NH$_2$), 3005 (—CH$_3$), 2920 (—CH$_2$), 1734 (—C=O), 1505 (—Ar).

Compound 93

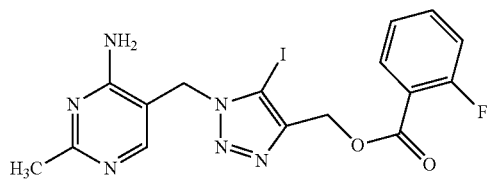 [SMILES: Cc1ncc(Cn2nnc(COC(=O)c3ccccc3F)c2I)c(N)n1]

The pure product as yellow solid was obtained with yield of 82%, and m.p. is 187-188° C.

Elementary Analysis/%:

Calculated value: C, 41.04; H, 3.01; N, 17.95.

Measured value: C, 41.05; H, 3.30; N, 18.18.

$^1$H NMR (400 MHz, DMSO-d$_6$): δ 2.31 (s, 3H, CH$_3$), 5.39 (s, 2H, CH$_2$), 5.60 (s, 2H, CH$_2$), 7.02 (s, 2H, NH$_2$), 7.34 (d, 2H, J=8.0 Hz, Ar—H), 7.69 (s, 1H, Ar—H), 7.87 (d, 1H, J=8.0 Hz, Ar—H), 8.26 (s, 1H, pyrimidine CH).

IR(KBr) υ (cm$^{-1}$): 3428 (—NH$_2$), 3015 (—CH$_3$), 2920 (—CH$_2$), 1716 (—C=O), 1500 (—Ar).

Compound 94

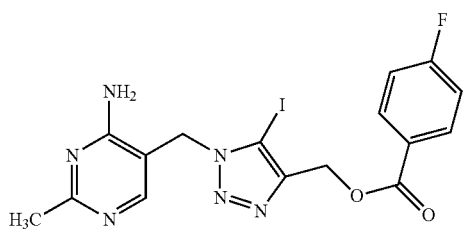 [SMILES: Cc1ncc(Cn2nnc(COC(=O)c3ccc(F)cc3)c2I)c(N)n1]

The pure product as yellow solid was obtained with yield of 73%, and m.p. is 207-209° C.

Elementary Analysis/%:

Calculated value: C, 41.04; H, 3.01; N, 17.95.

Measured value: C, 40.87; H, 3.42; N, 18.01.

$^1$H NMR (400 MHz, DMSO-d$_6$): δ 2.39 (s, 3H, CH$_3$), 5.42 (s, 2H, CH$_2$), 5.51 (s, 2H, CH$_2$), 6.95 (s, 2H, NH$_2$), 7.86 (d, 2H, J=16.0 Hz, Ar—H), 8.10 (s, 2H, Ar—H), 8.28 (s, 1H, pyrimidine CH).

IR(KBr) υ (cm$^{-1}$): 3437 (—NH$_2$), 3010 (—CH$_3$), 2920 (—CH$_2$), 1732 (—C=O), 1500 (—Ar), 1005 (—C—F).

Compound 95

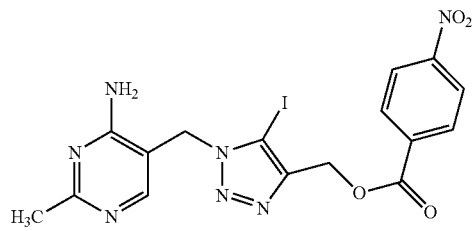 [SMILES: Cc1ncc(Cn2nnc(COC(=O)c3ccc([N+](=O)[O-])cc3)c2I)c(N)n1]

The pure product as yellow solid was obtained with yield of 86%, and m.p. is 192-193° C.

Elementary Analysis/%:

Calculated value: C, 38.80; H, 2.85; N, 19.80.

Measured value: C, 38.88; H, 3.01; N, 20.05.

$^1$H NMR (400 MHz, DMSO-d$_6$): δ 2.39 (s, 3H, CH$_3$), 5.36 (s, 2H, CH$_2$), 5.55 (s, 2H, CH$_2$), 6.98 (s, 2H, NH$_2$), 7.36 (s, 2H, Ar—H), 8.01 (s, 2H, Ar—H), 8.24 (s, 1H, pyrimidine CH).

IR(KBr) υ (cm$^{-1}$): 3422 (—NH$_2$), 3020 (—CH$_3$), 2920 (—CH$_2$), 1728 (—C=O), 1508 (—Ar), 1355 (—NO$_2$).

Compound 96

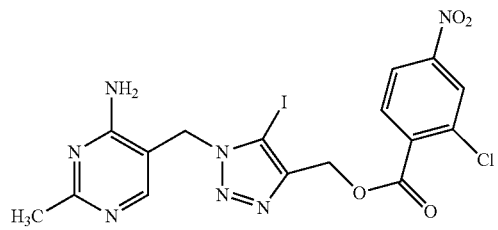 [SMILES: Cc1ncc(Cn2nnc(COC(=O)c3ccc([N+](=O)[O-])cc3Cl)c2I)c(N)n1]

The pure product as yellow solid was obtained with yield of 73%, and m.p. is 183-184° C.

Elementary Analysis/%:

Calculated value: C, 41.04; H, 3.01; N, 17.95.

Measured value: C, 40.87; H, 3.42; N, 18.01.

$^1$H NMR (400 MHz, DMSO-d$_6$): δ 2.31 (s, 3H, CH$_3$), 4.48 (s, 2H, CH$_2$), 5.47 (s, 2H, CH$_2$), 6.96 (s, 2H, NH$_2$), 8.28 (s, 1H, pyrimidine CH), 8.27-8.31 (m, 2H, Ar—H), 9.10 (s, 1H, Ar—H).

IR(KBr) υ (cm$^{-1}$): 3457 (—NH$_2$), 3010 (—CH$_3$), 2920 (—CH$_2$), 1647 (—C=O), 1508 (—Ar), 1355 (—NO$_2$).

EI-MS (m/z, %): 529 (M$^+$, 5).

Compound 97

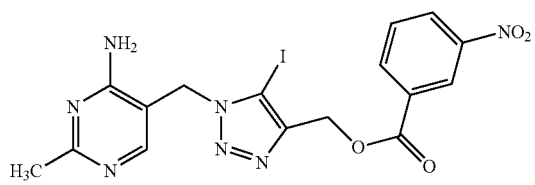

The pure product as yellow solid was obtained with yield of 78%, and m.p. is 201-202° C.

Elementary Analysis/%:

Calculated value: C, 38.80; H, 2.85; N, 19.80.

Measured value: C, 38.82; H, 2.75; N, 20.23.

¹H NMR (400 MHz, DMSO-d₆): δ 2.30 (s, 3H, CH₃), 5.45 (s, 2H, CH₂), 5.52 (s, 2H, CH₂), 7.00 (s, 2H, NH₂), 8.28 (s, 1H, pyrimidine CH), 8.07-8.10 (m, 2H, Ar—H), 8.36-8.38 (m, 2H, Ar—H).

IR(KBr) υ (cm⁻¹): 3381 (—NH₂), 3010 (—CH₃), 2920 (—CH₂), 1735 (—C═O), 1508 (—Ar), 1350 (—NO₂).

Compound 98

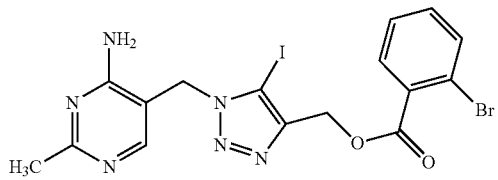

The pure product as yellow solid was obtained with yield of 96%, and m.p. is 200-202° C.

Elementary Analysis/%:

Calculated value: C, 36.32; H, 2.67; N, 15.88.

Measured value: C, 36.57; H, 2.63; N, 15.87.

¹H NMR (400 MHz, DMSO-d₆): δ 2.31 (s, 3H, CH₃), 5.36 (s, 2H, CH₂), 5.59 (s, 2H, CH₂), 7.00 (s, 2H, NH₂), 7.49 (s, 2H, Ar—H), 7.73 (s, 2H, Ar—H), 8.26 (s, 1H, pyrimidine CH).

IR(KBr) υ (cm⁻¹): 3414 (—NH₂), 3011 (—CH₃), 2923 (—CH₂), 1735 (—C═O), 1508 (—Ar).

Compound 99

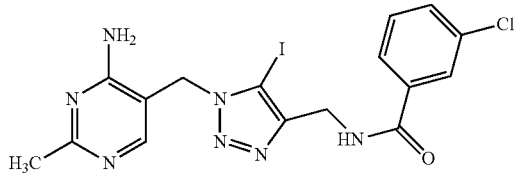 [SMILES: Cc1ncc(Cn2nnc(CNC(=O)c3cccc(Cl)c3)c2I)c(N)n1]

The pure product as yellow solid was obtained with yield of 59%, and m.p. is 197-198° C.

Elementary Analysis/%:

Calculated value: C, 39.79; H, 3.13; N, 20.27.

Measured value: C, 39.76; H, 3.38; N, 20.61.

¹H NMR (400 MHz, DMSO-d₆): δ 2.32 (s, 3H, CH₃), 4.49 (s, 2H, CH₂), 5.44 (s, 2H, CH₂), 6.94 (s, 2H, NH₂), 7.50 (d, 2H, J=3.2 Hz, Ar—H), 7.83 (d, 2H, J=4.0 Hz, Ar—H), 8.30 (s, 1H, pyrimidine CH).

IR(KBr) υ (cm⁻¹): 3363 (—NH₂), 3010 (—CH₃), 2920 (—CH₂), 1628 (—C═O), 1501 (—Ar).

Compound 100

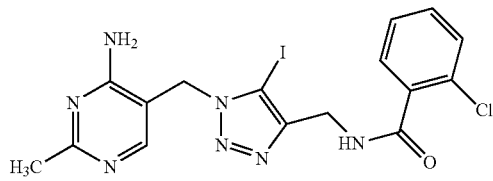

The pure product as yellow solid was obtained with yield of 45%, and m.p. is 186-188° C.

Elementary Analysis/%:

Calculated value: C, 39.79; H, 3.13; N, 20.27.

Measured value: C, 40.16; H, 3.39; N, 20.22.

¹H NMR (400 MHz, DMSO-d₆): δ 2.32 (s, 3H, CH₃), 4.49 (s, 2H, CH₂), 5.41 (s, 2H, CH₂), 6.91 (s, 2H, NH₂), 7.43-7.48 (m, 4H, Ar—H), 8.10 (s, 2H, Ar—H), 8.28 (s, 1H, pyrimidine CH).

IR(KBr) υ (cm⁻¹): 3456 (—NH₂), 3010 (—CH₃), 2920 (—CH₂), 1650 (—C═O), 1505 (—Ar).

Compound 101

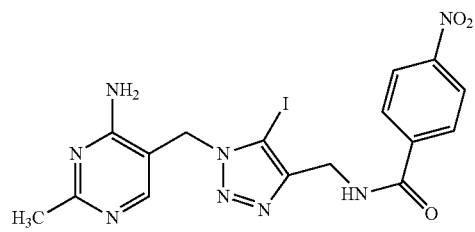 [SMILES: Cc1ncc(Cn2nnc(CNC(=O)c3ccc([N+](=O)[O-])cc3)c2I)c(N)n1]

The pure product as yellow solid was obtained with yield of 86%, and m.p. is 223-224° C.

Elementary Analysis/%:

Calculated value: C, 38.88; H, 3.06; N, 22.67.

Measured value: C, 39.25; H, 2.89; N, 22.96.

¹H NMR (400 MHz, DMSO-d₆): δ 2.30 (s, 3H, CH₃), 4.03 (s, 2H, CH₂), 4.95 (s, 2H, CH₂), 6.43 (s, 2H, NH₂), 7.59 (s, 2H, Ar—H), 7.81 (s, 2H, Ar—H), 8.26 (s, 1H, pyrimidine CH).

IR(KBr) υ (cm⁻¹): 3431 (—NH₂), 3010 (—CH₃), 2920 (—CH₂), 1648 (—C═O), 1505 (—Ar), 1346 (—NO₂).

Compound 102

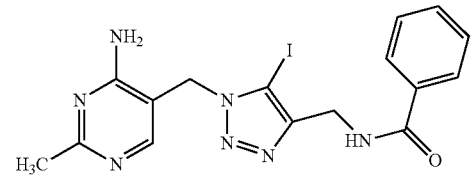 [SMILES: Cc1ncc(Cn2nnc(CNC(=O)c3ccccc3)c2I)c(N)n1]

The pure product as yellow solid was obtained with yield of 63%, and m.p. is 218-220° C.

Elementary Analysis/%:

Calculated value: C, 42.78; H, 3.59; N, 21.82.

Measured value: C, 42.93; H, 3.62; N, 21.65.

¹H NMR (400 MHz, DMSO-d₆): δ 2.30 (s, 3H, CH₃), 4.49 (s, 2H, CH₂), 5.41 (s, 2H, CH₂), 6.89 (s, 2H, NH₂), 7.48-7.52 (m, 5H, Ar—H), 8.28 (s, 1H, pyrimidine CH).

IR(KBr) υ (cm⁻¹): 3440 (—NH₂), 3010 (—CH₃), 2920 (—CH₂), 1644 (—C═O), 1505 (—Ar).

Compound 103

The pure product as yellow solid was obtained with yield of 84%, and m.p. is 231-233° C.

Elementary Analysis/%:

Calculated value: C, 39.79; H, 3.13; N, 20.27.

Measured value: C, 39.78; H, 2.73; N, 20.74.

$^1$H NMR (400 MHz, DMSO-d$_6$): δ 2.10 (s, 3H, CH$_3$), 4.50 (s, 2H, CH$_2$), 5.41 (s, 2H, CH$_2$), 6.90 (s, 2H, NH$_2$), 7.53 (d, 2H, J=8.0 Hz, Ar—H), 7.88 (d, 2H, J=12.0 Hz, Ar—H), 8.28 (s, 1H, pyrimidine CH).

IR(KBr) υ (cm$^{-1}$): 3425 (—NH$_2$), 3010 (—CH$_3$), 2920 (—CH$_2$), 1651 (—C=O), 1500 (—Ar).

Compound 104

The pure product as yellow solid was obtained with yield of 56%, and m.p. is 217-219° C.

Elementary Analysis/%:

Calculated value: C, 41.13; H, 3.24; N, 20.98.

Measured value: C, 41.26; H, 3.19; N, 21.04.

$^1$H NMR (400 MHz, DMSO-d$_6$): δ 2.09 (s, 3H, CH$_3$), 4.50 (s, 2H, CH$_2$), 5.47 (s, 2H, CH$_2$), 6.95 (s, 2H, NH$_2$), 7.28 (s, 2H, Ar—H), 7.93 (s, 2H, Ar—H), 8.28 (s, 1H, pyrimidine CH), 8.95 (s, 1H, NH).

IR(KBr) υ (cm$^{-1}$): 3429 (—NH$_2$), 3010 (—CH$_3$), 2920 (—CH$_2$), 1650 (—C=O), 1500 (—Ar).

Compound 105

The pure product as yellow solid was obtained with yield of 55%, and m.p. is 204-206° C.

Elementary Analysis/%:

Calculated value: C, 41.13; H, 3.24; N, 20.98.

Measured value: C, 41.26; H, 3.19; N, 21.04.

$^1$H NMR (400 MHz, DMSO-d$_6$): δ 2.31 (s, 3H, CH$_3$), 4.49 (s, 2H, CH$_2$), 5.49 (s, 2H, CH$_2$), 7.04 (s, 2H, NH$_2$), 7.21 (s, 2H, Ar—H), 7.56 (d, 2H, J=4.0 Hz, Ar—H), 8.28 (s, 1H, pyrimidine CH), 8.75 (s, 1H, NH).

IR(KBr) υ (cm$^{-1}$): 3347 (—NH$_2$), 3010 (—CH$_3$), 2920 (—CH$_2$), 1650 (—C=O), 1500 (—Ar), 1050 (—C—F).

Compound 106

The pure product as yellow solid was obtained with yield of 48%, and m.p. is 180-182° C.

Elementary Analysis/%:

Calculated value: C, 42.60; H, 3.79; N, 20.46.

Measured value: C, 42.90; H, 3.53; N, 20.32.

$^1$H NMR (400 MHz, DMSO-d$_6$): δ 2.27 (s, 3H, CH$_3$), 2.36 (s, 3H, CH$_3$), 4.45 (s, 2H, CH$_2$), 5.36 (s, 2H, CH$_2$), 6.90 (s, 2H, NH$_2$), 7.24 (s, 2H, Ar—H), 7.74 (d, 2H, J=4.0 Hz, Ar—H), 8.28 (s, 1H, pyrimidine CH), 8.93 (s, 1H, NH).

IR(KBr) υ (cm$^{-1}$): 3407 (—NH$_2$), 3010 (—CH$_3$), 2920 (—CH$_2$), 1686 (—C=O), 1502 (—Ar).

Compound 107

The pure product as yellow solid was obtained with yield of 63%, and m.p. is 183-184° C.

Elementary Analysis/%:

Calculated value: C, 38.88; H, 3.06; N, 22.67.

Measured value: C, 38.40; H, 3.35; N, 22.19.

$^1$H NMR (400 MHz, DMSO-d$_6$): δ 2.39 (s, 3H, CH$_3$), 5.42 (s, 2H, CH$_2$), 5.54 (s, 2H, CH$_2$), 6.92 (s, 2H, NH$_2$), 8.01 (s, 2H, Ar—H), 8.26 (s, 1H, Ar—H), 8.28 (s, 1H, pyrimidine CH), 8.86 (s, 1H, NH).

IR(KBr) υ (cm⁻¹): 3436 (—NH₂), 3010 (—CH₃), 2920 (—CH₂), 1745 (—C═O), 1524 (—Ar), 1355 (—NO₂).

Compound 108

The pure product as yellow solid was obtained with yield of 79%, and m.p. is 202-204° C.

¹H NMR (400 MHz, DMSO-d₆): δ 2.28 (s, 3H, CH₃), 4.53 (s, 2H, CH₂), 5.39 (s, 2H, CH₂), 6.94 (s, 2H, NH₂), 7.78 (s, 2H, Ar—H), 8.01 (s, 2H, Ar—H), 8.38 (s, 1H, pyrimidine CH).

IR(KBr) υ (cm⁻¹): 3405 (—NH₂), 3010 (—CH₃), 2920 (—CH₂), 1654 (—C═O), 1524 (—Ar), 1355 (—NO₂).

Compound 109

The pure product as yellow solid was obtained with yield of 90%, and m.p. is 200-202° C.

Elementary Analysis/%:
Calculated value: C, 36.39; H, 2.86; N, 18.56.
Measured value: C, 36.74; H, 2.77; N, 18.36.

¹H NMR (400 MHz, DMSO-d₆): δ 2.30 (s, 3H, CH₃), 4.45 (s, 2H, CH₂), 5.44 (s, 2H, CH₂), 6.94 (s, 2H, NH₂), 7.35-7.39 (m, 4H, Ar—H), 8.28 (s, 1H, pyrimidine CH), 8.94 (s, 1H, NH).

IR(KBr) υ (cm⁻¹): 3449 (—NH₂), 3010 (—CH₃), 2920 (—CH₂), 1641 (—C═O), 1524 (—Ar).

Embodiment 5

Preparation of Compound 54

1 mmol 2-methyl-4-amino-5-azidomethylpyrimidine and 1 mmol benzoylpropyne ester were dissolved in a solvent of 6 ml acetonitrile. 0.01 mmol blue vitriol and 0.1 mmol sodium ascorbate were added thereto respectively. The reaction liquid was stirred over night at 0-20° C., and a significant amount of white or greenish solid precipitated out. It was extracted in ethyl acetate, and the organic phase was dried over anhydrous sodium sulfate over night. The anhydrous sodium sulfate solid was removed, and the organic phase was precipitated and purified by column chromatography on silica gel (G type) with gradient elution (acetone:petroleum ether=1:1), to give the pure product as white solid, with yield of 53%, mp: 135-137° C.

Elementary Analysis/%:
Calculated value: C, 48.24; H, 3.81; N, 19.86.
Measured value: C, 47.75; H, 4.06; N, 19.63.

¹H NMR (600 MHz, DMSO-d₆): δ 2.31 (s, 3H, CH₃), 4.97 (s, 2H, CH₂), 5.24 (s, 2H, CH₂), 5.45 (s, 2H, CH₂), 6.96 (s, 2H, NH₂), 7.07 (d, 1H, Ar—H), 7.32-7.34 (t, 1H, Ar—H), 7.59 (d, 1H, Ar—H), 8.00 (s, 1H, 1,2,3-triazole-H), 8.17 (s, 1H, pyrimidine CH).

The compounds 55-67 were prepared in analogy to the compound 54, with its structural data identified as follows:

Compound 55

The pure product as white solid was obtained with yield of 73%, and m.p. is 163-165° C.

Elementary Analysis/%:
Calculated value: C, 53.67; H, 4.75; N, 20.86.
Measured value: C, 53.53; H, 5.00; N, 20.82.

¹H NMR (600 MHz, DMSO-d₆): δ 2.26 (s, 3H, CH₃), 2.31 (s, 3H, CH₃), 4.77 (s, 2H, CH₂), 5.23 (s, 2H, CH₂), 5.45 (s, 2H, CH₂), 6.94 (s, 2H, NH₂), 6.78 (d, 1H, Ar—H), 6.94 (t, 1H, Ar—H), 7.27-7.28 (d, 1H, Ar—H), 8.00 (s, 1H, triazole CH), 8.17 (s, 1H, pyrimidine CH).

Compound 56

The pure product as white solid was obtained with yield of 77%, and m.p. is 152-153° C.

Elementary Analysis/%:
Calculated value: C, 52.51; H, 4.41; N, 21.61.
Measured value: C, 52.39; H, 4.57; N, 21.62.

¹H NMR (600 MHz, DMSO-d₆): δ 2.31 (s, 3H, CH₃), 4.82 (s, 2H, CH₂), 5.23 (s, 2H, CH₂), 5.45 (s, 2H, CH₂), 6.95 (s, 2H, NH₂), 6.93 (s, 2H, Ar—H), 7.31-7.32 (d, 2H, Ar—H), 8.00 (s, 1H, triazole CH), 8.17 (s, 1H, pyrimidine CH).

Compound 57

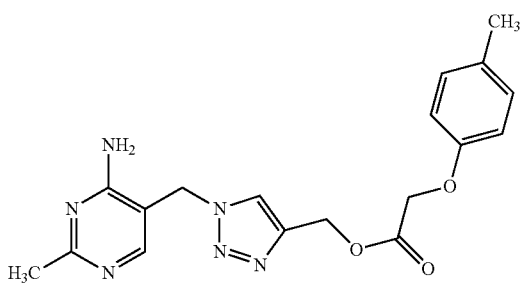 [SMILES: Cc1ccc(OCC(=O)OCc2cn(Cc3cnc(C)nc3N)nn2)cc1]

The pure product as white solid was obtained with yield of 65%, and m.p. is 149-151° C.
Elementary Analysis/%:
Calculated value: C, 58.69; H, 5.47; N, 22.81.
Measured value: C, 58.42; H, 5.75; N, 22.38.
$^1$H NMR (600 MHz, DMSO-$d_6$): δ 2.22 (s, 3H, CH$_3$), 2.31 (s, 3H, CH$_3$), 4.74 (s, 2H, CH$_2$), 5.22 (s, 2H, CH$_2$), 5.45 (s, 2H, CH$_2$), 6.96 (s, 2H, NH$_2$), 6.78-6.79 (t, 2H, Ar—H), 7.05-7.07 (t, 2H, Ar—H), 8.01 (s, 1H, triazole CH), 8.17 (s, 1H, pyrimidine CH).

Compound 58

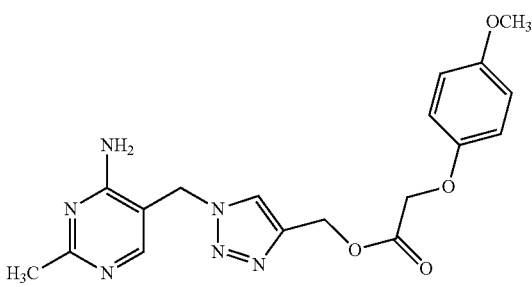 [SMILES: COc1ccc(OCC(=O)OCc2cn(Cc3cnc(C)nc3N)nn2)cc1]

The pure product as white solid was obtained with yield of 53%, and m.p. is 128-129° C.
Elementary Analysis/%:
Calculated value: C, 56.24; H, 5.24; N, 21.86.
Measured value: C, 56.47.42; H, 5.14; N, 22.05.
$^1$H NMR (600 MHz, DMSO-$d_6$): δ 2.22 (s, 3H, OCH$_3$), 2.31 (s, 3H, CH$_3$), 4.71 (s, 2H, CH$_2$), 5.22 (d, 2H, CH$_2$), 5.44 (s, 2H, CH$_2$), 6.96 (s, 2H, NH$_2$), 6.83 (s, 4H, Ar—H), 8.00 (s, 1H, triazole CH), 8.17 (s, 1H, pyrimidine CH).

Compound 59

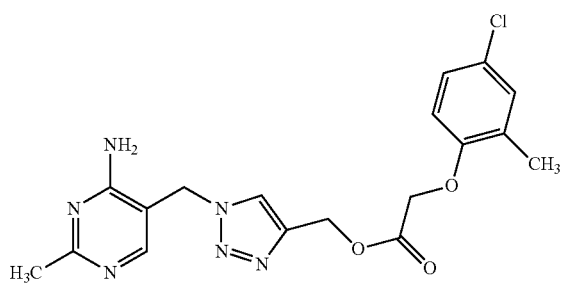

The pure product as white solid was obtained with yield of 53%, and m.p. is 138-140° C.
Elementary Analysis/%:
Calculated value: C, 53.67; H, 4.75; N, 20.86.
Measured value: C, 53.65; H, 5.10; N, 20.89.
$^1$H NMR (600 MHz, DMSO-$d_6$): δ 2.17 (s, 3H, CH$_3$), 2.31 (s, 3H, CH$_3$), 4.84 (s, 2H, CH$_2$), 5.22 (d, 2H, CH$_2$), 5.45 (s, 2H, CH$_2$), 6.96 (s, 2H, NH$_2$), 6.84 (d, 1H, Ar—H), 7.13-7.15 (t, 1H, Ar—H), 7.22 (s, 1H, Ar—H), 8.00 (s, 1H, triazole CH), 8.16 (s, 1H, pyrimidine CH).

Compound 60

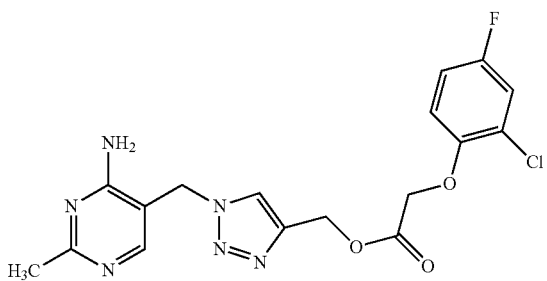 [SMILES: Cc1ncc(Cn2cc(COC(=O)COc3ccc(F)cc3Cl)nn2)c(N)n1]

The pure product as white solid was obtained with yield of 70%, and m.p. is 144-146° C.
Elementary Analysis/%:
Calculated value: C, 50.19; H, 3.96; N, 20.66.
Measured value: C, 50.62; H, 3.52; N, 20.80.
$^1$H NMR (600 MHz, DMSO-$d_6$): δ 2.31 (s, 3H, CH$_3$), 4.93 (s, 2H, CH$_2$), 5.24 (s, 2H, CH$_2$), 5.45 (s, 2H, CH$_2$), 6.96 (s, 2H, NH$_2$), 7.05-7.09 (m, 1H, Ar—H), 7.11-7.15 (m, 1H, Ar—H), 7.45 (q, 1H, Ar—H), 8.00 (s, 1H, triazole CH), 8.16 (s, 1H, pyrimidine CH).

Compound 61

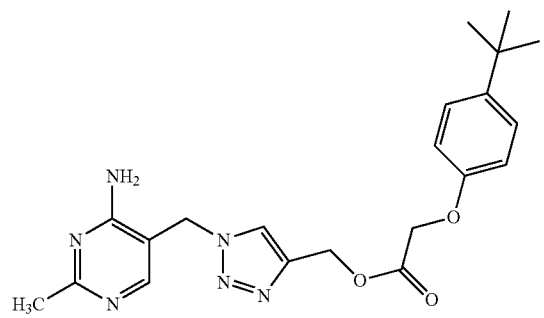 [SMILES: Cc1ncc(Cn2cc(COC(=O)COc3ccc(C(C)(C)C)cc3)nn2)c(N)n1]

The pure product as white solid was obtained with yield of 69%, and m.p. is 107-110° C.
Elementary Analysis/%:
Calculated value: C, 61.45; H, 6.38; N, 20.47.
Measured value: C, 61.60; H, 6.81; N, 20.40.
$^1$H NMR (600 MHz, DMSO-$d_6$): δ 1.24 (s, 9H, 3CH$_3$), 2.31 (s, 3H, CH$_3$), 4.75 (s, 2H, CH$_2$), 5.23 (s, 2H, CH$_2$), 5.45 (s, 2H, CH$_2$), 6.96 (s, 2H, NH$_2$), 6.81-6.82 (d, 2H, Ar—H), 7.27-7.28 (d, 2H, Ar—H), 8.00 (s, 1H, triazole CH), 8.18 (s, 1H, pyrimidine CH).

Compound 62

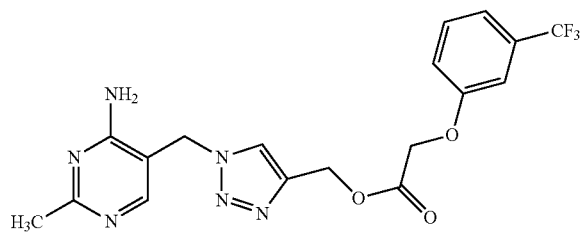 [SMILES: Cc1ncc(Cn2cc(COC(=O)COc3cccc(C(F)(F)F)c3)nn2)c(N)n1]

The pure product as white solid was obtained with yield of 49%, and m.p. is 138-140° C.

Elementary Analysis/%:

Calculated value: C, 51.19; H, 4.06; N, 19.90.

Measured value: C, 51.36; H, 3.66; N, 20.32.

$^1$H NMR (600 MHz, DMSO-$d_6$): δ 2.55 (s, 3H, CH$_3$), 4.68 (s, 2H, CH$_2$), 5.33-5.34 (d, 2H, CH$_2$), 5.63 (s, 2H, CH$_2$), 7.25 (s, 2H, NH$_2$), 7.04-7.07 (t, 2H, Ar—H), 7.25-7.27 (t, 1H, Ar—H), 7.37-7.39 (q, 1H, Ar—H), 7.61 (s, 1H, triazole CH), 8.18 (s, 1H, pyrimidine CH).

Compound 63

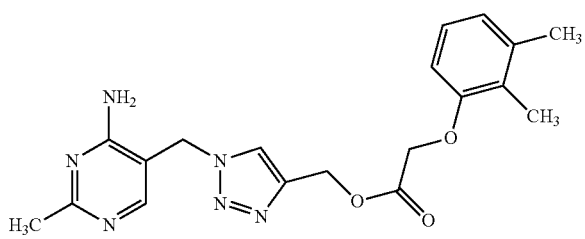

The pure product as white solid was obtained with yield of 72%, and m.p. is 168-171° C.

Elementary Analysis/%:

Calculated value: C, 59.67; H, 5.80; N, 21.98.

Measured value: C, 59.89; H, 5.60; N, 22.10.

$^1$H NMR (600 MHz, DMSO-$d_6$): δ 2.09 (s, 3H, CH$_3$), 2.21 (s, 2H, CH$_3$), 2.31 (s, 3H, CH$_3$), 4.77 (s, 2H, CH$_2$), 5.23 (s, 2H, CH$_2$), 5.44 (s, 2H, CH$_2$), 6.96 (s, 2H, NH$_2$), 6.64 (d, 1H, Ar—H), 6.76 (d, 1H, Ar—H), 6.97 (d, 1H, Ar—H), 8.01 (s, 1H, triazole CH), 8.15 (s, 1H, pyrimidine CH).

Compound 64

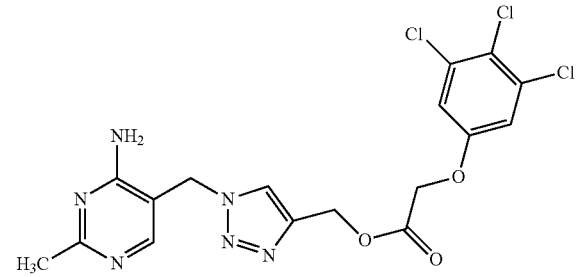 [SMILES: Cc1ncc(Cn2cc(COC(=O)COc3cc(Cl)c(Cl)c(Cl)c3)nn2)c(N)n1]

The pure product as white solid was obtained with yield of 58%, and m.p. is 160-161° C.

Elementary Analysis/%:

Calculated value: C, 44.61; H, 3.30; N, 18.36.

Measured value: C, 44.71; H, 3.39; N, 18.79.

$^1$H NMR (600 MHz, DMSO-$d_6$): δ 2.31 (s, 3H, CH$_3$), 5.03 (s, 2H, CH$_2$), 5.24 (s, 2H, CH$_2$), 5.45 (s, 2H, CH$_2$), 6.96 (s, 2H, NH$_2$), 7.45 (s, 1H, Ar—H), 7.83 (s, 1H, Ar—H), 8.01 (s, 1H, triazole CH), 8.17 (s, 1H, pyrimidine CH).

Compound 65

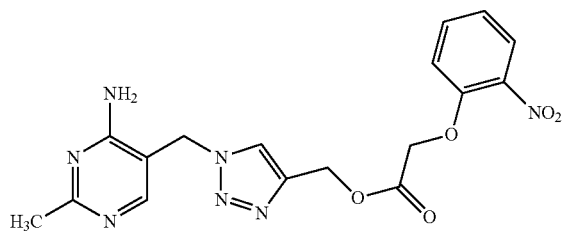 [SMILES: Cc1ncc(Cn2cc(COC(=O)COc3ccccc3[N+](=O)[O-])nn2)c(N)n1]

The pure product as white solid was obtained with yield of 77%, and m.p. is 158-160° C.

Elementary Analysis/%:

Calculated value: C, 51.13; H, 4.29; N, 24.55.

Measured value: C, 50.62; H, 4.61; N, 24.20.

$^1$H NMR (600 MHz, DMSO-$d_6$): δ 2.30 (s, 3H, CH$_3$), 5.04 (s, 2H, CH$_2$), 5.22 (s, 2H, CH$_2$), 5.44 (s, 2H, CH$_2$), 6.96 (s, 2H, NH$_2$), 7.13 (t, 1H, Ar—H), 7.23 (d, 1H, Ar—H), 7.57 (t, 1H, Ar—H), 7.85 (d, 1H, Ar—H), 8.00 (s, 1H, triazole CH), 8.15 (s, 1H, pyrimidine CH).

Compound 66

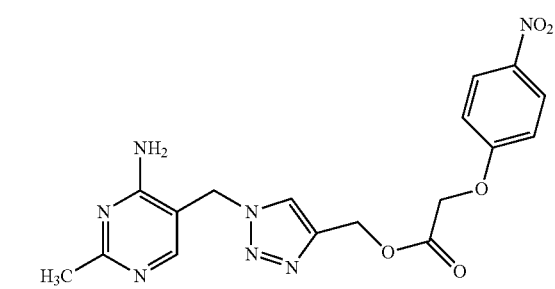

The pure product as white solid was obtained with yield of 56%, and m.p. is 145-148° C.

Elementary Analysis/%:

Calculated value: C, 51.13; H, 4.29; N, 24.55.

Measured value: C, 50.64; H, 4.67; N, 24.29.

$^1$H NMR (600 MHz, DMSO-$d_6$): δ 2.30 (s, 3H, CH$_3$), 5.02 (s, 2H, CH$_2$), 5.24 (s, 2H, CH$_2$), 5.45 (s, 2H, CH$_2$), 6.96 (s, 2H, NH$_2$), 7.14 (d, 2H, Ar—H), 8.19-8.20 (d, 2H, Ar—H), 8.00 (s, 1H, triazole CH), 8.17 (s, 1H, pyrimidine CH).

Compound 67

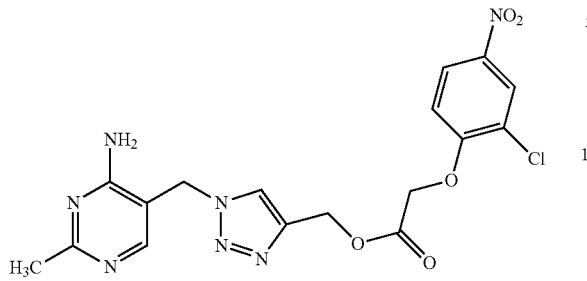

The pure product as white solid was obtained with yield of 56%, and m.p. is 145-148° C.

Elementary Analysis/%:

Calculated value: C, 47.07; H, 3.72; N, 22.60.

Measured value: C, 47.26; H, 3.83; N, 22.19.

$^1$H NMR (600 MHz, DMSO-d$_6$): δ 2.30 (s, 3H, CH$_3$), 5.16 (s, 2H, CH$_2$), 5.24 (s, 2H, CH$_2$), 5.45 (s, 2H, CH$_2$), 6.96 (s, 2H, NH$_2$), 7.30 (d, 1H, Ar—H), 7.98 (s, 1H, triazole CH), 8.17 (s, 1H, pyrimidine CH), 8.18 (t, 1H, Ar—H), 8.34 (d, 1H, Ar—H).

Embodiment 6

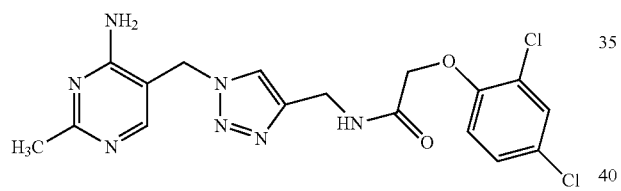

Preparation of Compound 68

1 mmol 2-methyl-4-amino-5-azidomethylpyrimidine and 1 mmol iodo-4-nitrophenoxypropyne were dissolved in 5 ml anhydrous tetrahydrofuran. 0.05 mmol CuBr and 2 mmol triethylamine were added respectively thereto, and stirred for 12 hours at 50-60° C. Upon addition of water at stirring, the solid precipitated out. The solid precipitant was filtered by suction, and dried to give the off-white solid, with yield of 85%, and m.p. is 201-202° C.

Elementary Analysis/%:

Calculated value: C, 48.35; H, 4.06; N, 23.22.

Measured value: C, 48.73; H, 4.38; N, 23.11.

$^1$H NMR (600 MHz, DMSO-d$_6$): δ 2.31 (s, 3H, CH$_3$), 4.34-4.36 (d, 2H, J=8.4 Hz, CH$_2$—NH), 4.64 (s, 2H, CH$_2$), 5.41 (s, 2H, CH$_2$), 6.95 (s, 2H, NH$_2$), 6.99 (s, 1H, CH), 7.01 (s, 1H, Ar—H), 7.33-7.35 (dd, 1H, J=3.6 Hz, 9.6 Hz, Ar—H), 7.58-7.59 (d, 1H, J=4.2 Hz, Ar—H), 7.95 (s, 1H, pyrimidine CH), 8.55 (s, 1H, NH).

$^{13}$C NMR (100 MHz, DMSO-d$_6$) δ(ppm): 25.2, 46.7, 56.7, 58.2, 108.4, 114.7, 124.8, 127.1, 129.6, 130.4, 134.7, 138.5, 142.0, 156.1, 161.2, 165.1, 167.7.

The compounds 69-79 were prepared in analogy to the compound 68, with its structural data identified as follows:

Compound 69

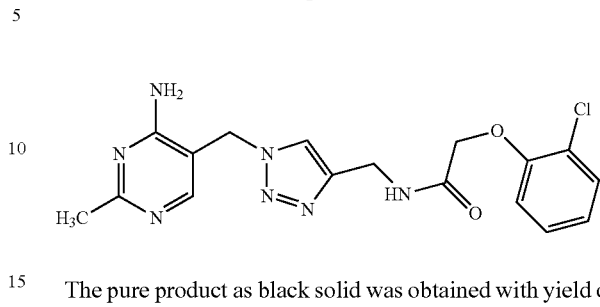

The pure product as black solid was obtained with yield of 78%, and m.p. is 201-202° C.

Elementary Analysis/%:

Calculated value: C, 52.65; H, 4.68; N, 25.28.

Measured value: C, 52.53; H, 4.72; N, 25.39.

$^1$H NMR (600 MHz, DMSO-d$_6$): δ 2.30 (s, 3H, CH$_3$), 4.35 (s, 2H, CH$_2$), 4.64 (s, 2H, CH$_2$), 5.46 (s, 2H, CH$_2$), 6.95 (s, 2H, NH$_2$), 6.96-6.97 (m, 2H, Ar—H), 7.33-7.34 (m, 2H, Ar—H), 7.49 (s, 2H), 8.86 (s, 1H, NH).

$^{13}$C NMR (100 MHz, DMSO-d$_6$) δ(ppm): 25.0, 46.1, 57.2, 60.3, 107.9, 115.6, 124.7, 127.0, 129.6, 130.3, 134.6, 138.4, 143.0, 165.5, 161.4, 164.2, 165.9.

Compound 70

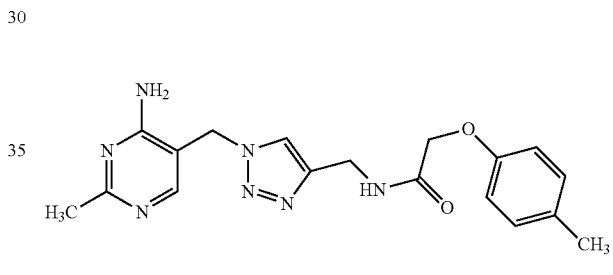

The pure product as off-white solid was obtained with yield of 74%, and m.p. is 117-119° C.

Elementary Analysis/%:

Calculated value: C, 58.84; H, 5.76; N, 26.69.

Measured value: C, 58.93; H, 5.82; N, 26.90.

$^1$H NMR (600 MHz, DMSO-d$_6$): δ 2.22 (s, 3H, CH$_3$), 2.29 (s, 3H, CH$_3$), 4.34-4.35 (d, 2H, J=5.4 Hz, CH$_2$—NH), 4.43 (s, 2H, CH$_2$), 5.39 (s, 2H, CH$_2$), 6.81-6.82 (d, 2H, J=8.4 Hz, Ar—H), 6.94 (s, 2H, NH$_2$), 7.06-7.07 (d, 2H, J=8.4 Hz, Ar—H), 7.91 (s, 1H, CH), 7.98 (s, 1H, CH), 8.61 (s, 1H, NH).

$^{13}$C NMR (100 MHz, DMSO-d$_6$) δ(ppm): 20.2, 24.5, 34.3, 46.9, 66.5, 108.8, 114.8, 116.5, 123.0, 129.8, 145.5, 155.5, 156.4, 161.1, 167.1, 168.8.

Compound 71

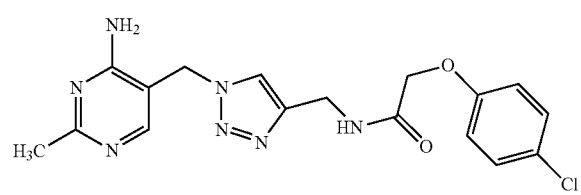 [SMILES: Cc1ncc(Cn2cc(CNC(=O)COc3ccc(Cl)cc3)nn2)c(N)n1]

The pure product as grey solid was obtained with yield of 61%, and m.p. is 124-125° C.
Elementary Analysis/%:
Calculated value: C, 52.65; H, 4.68; N, 25.28.
Measured value: C, 52.68; H, 5.04; N, 25.78.
$^1$H NMR (600 MHz, DMSO-$d_6$): δ 2.30 (s, 3H, $CH_3$), 4.34 (s, 2H, $CH_2$), 4.49 (s, 2H, $CH_2$), 5.41 (s, 2H, $CH_2$), 6.95-6.96 (d, 4H, J=7.8 Hz), 7.32-7.33 (d, 2H, J=7.2 Hz, Ar—H), 7.94 (s, 1H), 8.86 (s, 1H, NH).
$^{13}$C NMR (100 MHz, DMSO-$d_6$) δ(ppm): 25.3, 47.0, 57.4, 67.1, 107.7, 124.3, 126.8, 128.3, 130.6, 138.1, 141.3, 157.9, 160.7, 164.3, 167.3.

Compound 72

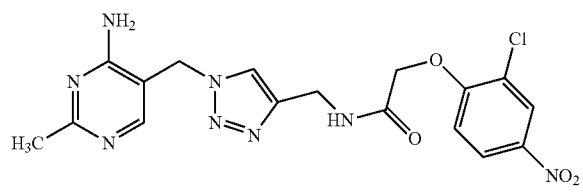 [SMILES: Cc1ncc(Cn2cc(CNC(=O)COc3ccc([N+](=O)[O-])cc3Cl)nn2)c(N)n1]

The pure product as grey solid was obtained with yield of 91%, and m.p. is 183-184° C.
Elementary Analysis/%:
Calculated value: C, 47.17; H, 3.96; N, 25.89.
Measured value: C, 47.18; H, 3.88; N, 25.54.
$^1$H NMR (600 MHz, DMSO-$d_6$): δ 2.29 (s, 3H, $CH_3$), 4.35-4.36 (d, 2H, J=5.4 Hz, $CH_2$), 4.85 (s, 2H, $CH_2$), 5.41 (s, 2H, $CH_2$), 6.93 (s, 2H, $NH_2$), 7.19-7.20 (d, 1H, 9.6 Hz, Ar—H), 7.96 (s, 1H, CH), 8.19-8.19 (d, 1H, J=2.4 Hz, Ar—H), 8.20 (s, 1H, CH), 8.32-8.33 (d, 1H, J=2.4 Hz, Ar—H), 8.65 (s, 1H, NH).
$^{13}$C NMR (100 MHz, DMSO-$d_6$) δ(ppm): 24.9, 32.9, 45.9, 67.3, 107.8, 113.4, 115.1, 122.3, 124.6, 129.1, 132.8, 144.3, 155.5, 155.9, 160.2, 166.5, 167.9.

Compound 73

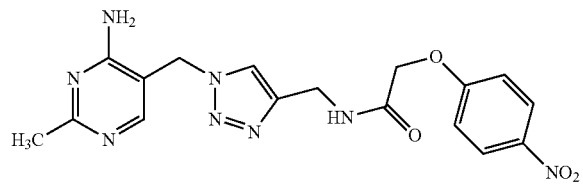 [SMILES: Cc1ncc(Cn2cc(CNC(=O)COc3ccc([N+](=O)[O-])cc3)nn2)c(N)n1]

The pure product as brown solid was obtained with yield of 71%, and m.p. is 143-144° C.
Elementary Analysis/%:
Calculated value: C, 51.25; H, 4.55; N, 28.13.
Measured value: C, 51.62; H, 4.89; N, 27.89.
$^1$H NMR (600 MHz, DMSO-$d_6$): δ 2.29 (s, 3H, $CH_3$), 4.35-4.36 (d, 2H, J=4.8 Hz, $CH_2$), 4.69 (s, 2H, $CH_2$), 5.41 (s, 2H, $CH_2$), 6.93 (s, 2H, $NH_2$), 7.13-7.14 (d, 2H, J=9.0 Hz, Ar—H), 7.95 (s, 1H, CH), 8.20-8.22 (d, 2H, J=9.0 Hz, Ar—H), 8.77 (s, 1H, NH).
$^{13}$C NMR (100 MHz, DMSO-$d_6$) δ(ppm): 24.5, 45.8, 57.0, 66.7, 107.3, 124.9, 127.3, 128.8, 130.8, 137.5, 141.5, 155.6, 160.9, 163.5, 166.1.
MS (EI) m/z (%): 398 ($M^+$, 4).

Compound 74

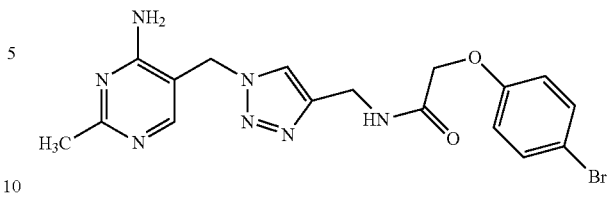

The pure product as brown solid was obtained with yield of 85%, and m.p. is 105-106° C.
Elementary Analysis/%:
Calculated value: C, 47.23; H, 4.20; N, 22.68.
Measured value: C, 47.52; H, 4.58; N, 22.37.
$^1$H NMR (600 MHz, DMSO-$d_6$): δ 2.29 (s, 3H, $CH_3$), 4.34-4.35 (d, 2H, J=5.4 Hz, $CH_2$), 4.49 (s, 2H, $CH_2$), 5.39 (s, 2H, $CH_2$), 6.90-6.91 (d, 4H, J=8.4 Hz), 7.44-7.45 (d, 2H, J=8.4 Hz, Ar—H), 7.93 (s, 1H), 8.67 (s, 1H, NH).
$^{13}$C NMR (100 MHz, DMSO-$d_6$) δ(ppm): 25.7, 46.6, 58.9, 56.6, 108.4, 124.8, 128.3, 129.0, 131.1, 138.4, 141.6, 156.5, 161.7, 164.5, 167.0.
MS (EI) m/z (%): 432 ($M^+$, 15).

Compound 75

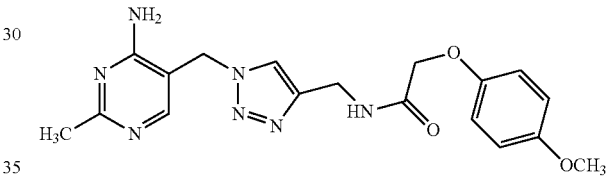

The pure product as brown solid was obtained with yield of 66%, and m.p. is 165-166° C.
Elementary Analysis/%:
Calculated value: C, 56.39; H, 5.52; N, 25.57.
Measured value: C, 56.35; H, 5.67; N, 25.85.
$^1$H NMR (600 MHz, DMSO-$d_6$): δ 2.30 (s, 3H, $CH_3$), 3.68 (s, 3H, OCH3), 4.34 (s, 2H, CH2), 4.41 (s, 2H, CH2), 5.40 (s, 2H, CH2), 6.85-6.87 (d, 5H, J=12.0 Hz), 6.95 (s, 1H, Ar—H), 8.03 (s, 1H), 8.60 (s, 1H, NH).
IR (KBr) υ ($cm^{-1}$): 3441 (—$NH_2$), 2950 (—$CH_3$), 2850 ($CH_2$), 1644 (—C=O), 1505 (—Ar).

Compound 76

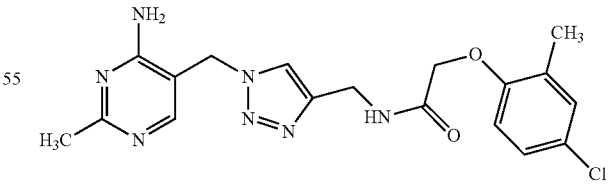

The pure product as brown solid was obtained with yield of 57%, and m.p. is and m.p. is 177-178° C.
Elementary Analysis/%:
Calculated value: C, 53.80; H, 5.02; N, 24.40.
Measured value: C, 53.77; H, 5.15; N, 24.56.
$^1$H NMR (600 MHz, DMSO-$d_6$): δ 2.26 (s, 3H, $CH_3$), 2.29 (s, 3H, $CH_3$), 4.34 (s, 2H, $CH_2$), 4.47 (s, 2H, $CH_2$), 5.39 (s, 2H, CH₂), 6.77-6.79 (d, 1H, J=7.8 Hz, Ar—H), 6.94 (s, 3H), 7.28-7.29 (d, 2H, J=9.0 Hz, Ar—H), 7.93 (s, 1H), 8.64 (s, 1H, NH).

IR(KBr) υ (cm⁻¹): 3446 (—NH₂), 2950 (—CH₃), 2850 (CH₂), 1660 (—C=O), 1505 (—Ar).

Compound 77

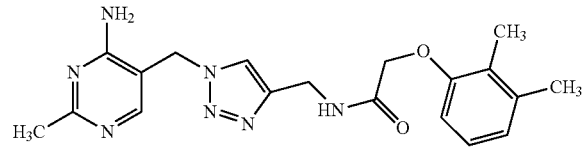

The pure product as yellow solid was obtained with yield of 57%, and m.p. is 169-170° C.

Elementary Analysis/%:
Calculated value: C, 59.83; H, 6.08; N, 25.70.
Measured value: C, 60.26; H, 6.02; N, 25.41.

¹H NMR (600 MHz, DMSO-d₆): δ 2.01 (s, 3H, CH₃), 2.20 (s, 3H, CH₃), 2.29 (s, 3H, CH₃), 4.35-4.36 (s, 2H, J=6.0 Hz, CH₂), 4.46 (s, 2H, CH₂), 5.41 (s, 2H, CH₂), 6.63-6.64 (d, 1H, J=8.4 Hz, Ar—H), 6.76-6.77 (d, 1H, J=7.2 Hz), 6.94-6.98 (m, 3H), 7.89 (s, 1H), 8.47 (s, 1H, NH).

IR(KBr) υ (cm⁻¹): 3439 (—NH₂), 2950 (—CH₃), 2850 (—CH₂), 1675 (—C=O), 1505 (—Ar).

Compound 78

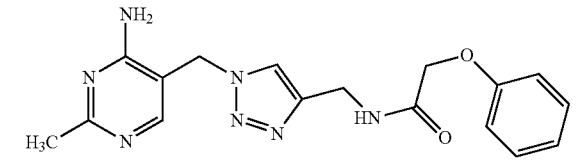 [SMILES: Cc1ncc(Cn2cc(CNC(=O)COc3ccccc3)nn2)c(N)n1]

The pure product as brown solid was obtained with yield of 71%, and m.p. is 168-169° C.

Elementary Analysis/%:
Calculated value: C, 57.78; H, 5.42; N, 27.75.
Measured value: C, 57.53; H, 5.24; N, 27.64.

¹H NMR (600 MHz, DMSO-d₆): δ 2.30 (s, 3H, CH₃), 4.34 (s, 2H, J=6.0 Hz, CH₂), 4.49 (s, 2H, CH₂), 5.41 (s, 2H, CH₂), 6.94-6.96 (m, 5H), 7.33-7.34 (m, 2H), 7.94 (s, 1H), 8.67 (s, 1H, NH).

IR(KBr) υ (cm⁻¹): 3447 (—NH₂), 2950 (—CH₃), 2850 (—CH₂), 1665 (—C=O), 1505 (—Ar).

Compound 79

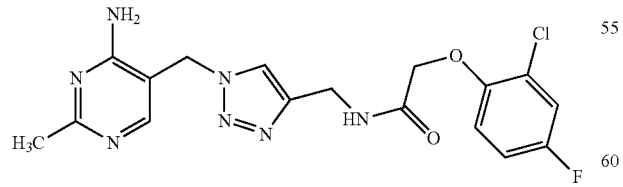

The pure product as brown solid was obtained with yield of 52%, and m.p. is 125-126° C.

Elementary Analysis/%:
Calculated value: C, 50.31; H, 4.22; N, 24.16.
Measured value: C, 50.10; H, 4.63; N, 23.59.

¹H NMR (600 MHz, DMSO-d₆): δ 2.30 (s, 3H, CH₃), 4.35 (s, 2H, J=6.0 Hz, CH₂), 4.48 (s, 2H, CH₂), 5.41 (s, 2H, CH₂), 6.95 (s, 2H), 7.20 (s, 2H), 7.42-7.43 (d, 2H, J=7.2 Hz), 7.93 (s, 1H), 8.52 (s, 1H, NH).

IR(KBr) υ (cm⁻¹): 3427 (—NH₂), 2964 (—CH₃), 2850 (CH₂), 1665 (—C=O), 1505 (—Ar), 1069 (—C—F).

TABLE 1

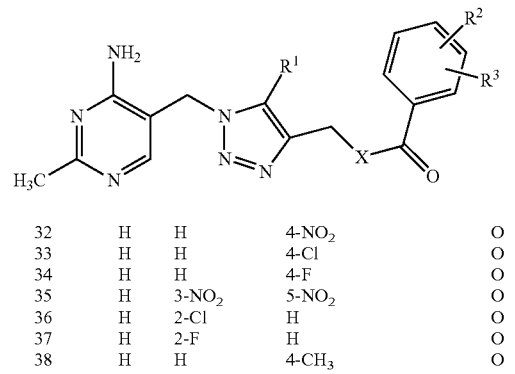

| No. | R¹ | R² | R³ | X |
|---|---|---|---|---|
| | | | | I-1 |
| 1 | H | H | 4-NO₂ | O |
| 2 | H | H | 4-Cl | O |
| 3 | H | H | 4-CO₂Et | O |
| 4 | H | H | 3-CF₃ | O |
| 5 | H | 2-Cl | 5-CH₃ | O |
| 6 | H | 2-Cl | 4-F | O |
| 7 | H | H | 4-COOH | O |
| 8 | H | 2-NO₂ | 4-NO₂ | O |
| 9 | H | H | 4-CH₂CO₂Me | O |
| 10 | H | 2-Cl | 4-Cl | O |
| 11 | H | 3-CH₃ | 4-Cl | O |
| 12 | H | H | H | O |
| 13 | H | H | 4-OCH₃ | O |
| 14 | H | 2-CH₃ | 3-CH₃ | O |
| 15 | H | 2-Cl | 4-NO₂ | O |
| 16 | H | 2-NO₂ | H | O |
| 17 | H | H | 4-CH₃ | O |
| 18 | H | 2-CH₃ | H | O |
| 19 | H | 3-CH₃ | H | O |
| 20 | H | H | 4-F | O |
| 21 | H | H | 4-Br | O |
| 22 | H | H | 4-CN | O |
| 23 | I | H | H | O |
| 24 | I | H | 4-NO₂ | O |
| 25 | I | 3-CH₃ | 4-Cl | O |
| 26 | I | H | 4-OCH₃ | O |
| 27 | I | 2-Cl | 4-F | O |
| 28 | I | H | 4-Cl | O |
| 29 | I | 2-CH₃ | 4-Cl | O |
| 30 | I | 2-Cl | 4-NO₂ | O |
| 31 | I | H | 4-CN | O |
| 80 | I | 2-NO₂ | H | O |
| 81 | I | H | 3-CF₃ | O |
| 82 | I | H | 4-F | O |
| 83 | I | 2-Cl | 4-Cl | O |
| 84 | I | H | 4-Br | O |
| 85 | I | 2-Br | H | O |
| 86 | I | 2-Cl | H | O |
| 87 | I | H | 4-CO₂Et | O |
| | | | | I-2 |
| 32 | H | H | 4-NO₂ | O |
| 33 | H | H | 4-Cl | O |
| 34 | H | H | 4-F | O |
| 35 | H | 3-NO₂ | 5-NO₂ | O |
| 36 | H | 2-Cl | H | O |
| 37 | H | 2-F | H | O |
| 38 | H | H | 4-CH₃ | O |

TABLE 1-continued

Synthsized compounds

| No. | R¹ | R² | R³ | X |
|---|---|---|---|---|
| 39 | H | 3-Cl | H | O |
| 40 | H | 2-Br | H | O |
| 41 | H | 3-NO₂ | H | O |
| 42 | H | 2-Cl | 4-NO₂ | O |
| 43 | H | H | H | NH |
| 44 | H | H | 4-F | NH |
| 45 | H | H | 4-CH₃ | NH |
| 46 | H | 2-F | H | NH |
| 47 | H | H | 4-NO₂ | NH |
| 48 | H | H | 4-Cl | NH |
| 49 | H | 2-Cl | H | NH |
| 50 | H | 3-Cl | H | NH |
| 51 | H | 2-Cl | 4-NO₂ | NH |
| 52 | H | 2-Br | H | NH |
| 53 | H | 3-NO₂ | H | NH |
| 88 | I | H | H | O |
| 89 | I | 2-Cl | H | O |
| 90 | I | 3-Cl | H | O |
| 91 | I | 4-Cl | H | O |
| 92 | I | 4-CH₃ | H | O |
| 93 | I | 2-F | H | O |
| 94 | I | 4-F | H | O |
| 95 | I | 4-NO₂ | H | O |
| 96 | I | 2-Cl | 4-NO₂ | O |
| 97 | I | 3-NO₂ | H | O |
| 98 | I | 2-Br | H | O |
| 99 | I | 3-Cl | H | NH |
| 100 | I | 2-Cl | H | NH |
| 101 | I | 4-NO₂ | H | NH |
| 102 | I | H | H | NH |
| 103 | I | 4-Cl | H | NH |
| 104 | I | 4-F | H | NH |
| 105 | I | 2-F | H | NH |
| 106 | I | 4-CH₃ | H | NH |
| 107 | I | 2-Cl | 4-NO₂ | NH |
| 108 | I | 3-NO₂ | H | NH |
| 109 | I | 2-Br | H | NH |

I-3

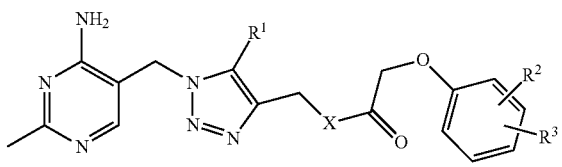

| | | | | |
|---|---|---|---|---|
| 54 | H | 2-Cl | 4-Cl | O |
| 55 | H | 3-CH₃ | 4-Cl | O |
| 56 | H | H | 4-Cl | O |
| 57 | H | H | 4-CH₃ | O |
| 58 | H | H | 4-CH₃O | O |
| 59 | H | 2-CH₃ | 4-Cl | O |
| 60 | H | 2-Cl | 4-F | O |
| 61 | H | H | 4-C(CH₃)₃ | O |
| 62 | H | 3-CF₃ | H | O |
| 63 | H | 2-CH₃ | 3-CH₃ | O |
| 64 | H | 3-Cl | 4,5-2Cl | O |
| 65 | H | 2-NO₂ | H | O |
| 66 | H | H | 4-NO₂ | O |
| 67 | H | 2-Cl | 4-NO₂ | O |
| 68 | H | 2-Cl | 4-Cl | NH |
| 69 | H | 2-Cl | H | NH |
| 70 | H | H | 4-CH₃ | NH |
| 71 | H | H | 4-Cl | NH |
| 72 | H | 2-Cl | 4-NO₂ | NH |
| 73 | H | H | 4-NO₂ | NH |
| 74 | H | H | 4-Br | NH |
| 75 | H | H | 4-OCH₃ | NH |
| 76 | H | 2-CH₃ | 4-Cl | NH |
| 77 | H | 2-CH₃ | 3-CH₃ | NH |
| 78 | H | H | H | NH |
| 79 | H | 2-Cl | 4-F | NH |

In the table, Me—methyl, Et—ethyl.

The compounds of general formula I according to the present invention have superior microbicidal activity against bacterial spot of cucumber, tomato bacterial leaf spot, *corynespora* leaf spot of cucumber, downy mildew of cucumber, rice sheath blight disease, wheat scab, early blight of tomato, gray mold of cucumber, tobacco brown spot and anthracnose of cucumber, some of which have equivalent or better controlling effects against bacteria or fungi than the commercial microbicides as control.

Embodiment 7

Testing of Microbicidal Activity

Testing Materials: Strain: Cucumber Angular Leaf Spot

Testing method: a cucumber seedling at the stage of 2 seminal leaves was inoculated by spraying a suspension of Cucumber Angular Leaf Spot. Testing agents and control agents were sprayed uniformly on the seminal leaves at A.M. of a sunshine day respectively. After 2 hours, the leaves were inoculated with pathogenic microbes and cultured at humidity. After full occurrence of disease in control group, state of illness was examined according to grading standards, and the controlling effects were measured. Testing results were given in table 2.

TABLE 2

Testing results from some compounds
(testing concentration of 500 μg/g)

| Compounds | Cucumber bacterial spot (%) |
|---|---|
| 32 | 60 |
| 33 | 60 |
| 34 | 60 |
| 35 | 45 |
| 36 | 60 |
| 37 | 70 |
| 38 | 60 |
| 39 | 60 |
| Zhongshengmycin | 70.69 |
| Bismerthiazol | 73.14 |
| Thiodiazole-copper | 65.89 |

Embodiment 8

Testing of Microbicidal Activity

Testing Materials: Strains: Tomato Bacterial Leaf Spot (Pseudomonassyringaepv. tomato (Okabe) Young, Dye & Wilkie), Cucumber Angular Leaf Spot, Rice Sheath Blight Disease (*Rhizoctonia solani*), *Corynespora* Leaf Spot of Cucumber (*Corynespora cassiicola*), Downy Mildew of Cucumber (Cucumber Downy Mildew).

Testing Method:

A cucumber seedling at the stage of 2 seminal leaves and a tomato seedling at the stage of 5 leaves were inoculated by spraying a suspension of spore for Downy Mildew of Cucumber and *Corynespora* Leaf Spot of Cucumber, and spraying a bacterial suspension for Cucumber Angular Leaf Spot and Tomato Bacterial Leaf Spot. Testing agents and control agents were sprayed uniformly at A.M. of a sunshine day on the cucumber seminal leaves. After 2 hours, the leaves were inoculated with pathogenic microbes and cultured at humidity. Inoculation of the suspension of spore by root irrigation is used for *fusarium* wilt of cucumber. Strip inoculation is used for Rice Sheath Blight Disease and *phytophthora* blight of pepper, in which the liquor was sprayed and after 2 hours, inoculation of strips was performed followed by culturing at humidity. After full occurrence of diseases in the control group, state of illness was examined according to grading standards, and a disease index and inhibition rate were calculated. Testing results were given in table 3.

TABLE 3

Testing results from some compounds (testing concentration of 500 μg/g)

| Compounds | Tomato Bacterial Leaf Spot Average inhibition rate (%) | Cucumber Angular Leaf Spot Average inhibition rate (%) | Rice Sheath Blight Disease Average inhibition rate (%) | Corynespora Leaf Spot of Cucumber Average inhibition rate (%) | Downy Mildew of Cucumber Average inhibition rate (%) |
|---|---|---|---|---|---|
| 1 | N | 60 | 90 | 50 | 75 |
| 2 | N | 60 | 80 | 55 | 75 |
| 3 | N | 60 | 80 | 80 | 60 |
| 4 | N | 60 | 60 | 70 | 35 |
| 5 | N | 50 | 80 | 70 | 70 |
| 6 | N | 65 | 70 | 90 | 30 |
| 7 | N | 55 | 70 | 70 | 40 |
| 8 | N | 60 | 70 | 70 | 60 |
| 9 | N | 60 | 90 | 60 | 80 |
| 10 | N | 60 | 70 | 70 | 50 |
| 11 | N | 60 | 70 | 65 | 50 |
| 12 | N | 60 | 80 | 70 | 70 |
| 13 | N | 60 | 70 | 80 | 50 |
| 14 | N | 60 | 70 | 90 | 35 |
| 15 | N | 60 | 60 | 80 | 30 |
| 16 | N | 70 | 70 | 80 | 50 |
| 32 | 70 | N | 60 | N | N |
| 33 | 70 | N | 55 | N | N |
| 34 | 60 | N | 40 | N | N |
| 35 | 80 | 80 | 50 | N | N |
| 36 | 80 | 60 | 45 | N | N |
| 37 | 70 | 37 | 50 | N | N |
| 38 | 95 | 40 | 50 | N | N |
| 39 | 80 | 10 | 60 | N | N |
| Thiophanate-methyl | N | | 85 | 80 | 20 |
| Zhongshengmycin | 60 | 70 | 50 | 50 | 40 |
| jingangmycin | N | | 70 | 70 | 70 |
| Dimethomorph | N | | 90 | 70 | 90 |
| Bismerthiazol | | 73 | | | |
| Thiodiazole-copper | | 66 | | | |

Note:
N represents undetermined activity.

Embodiment 9

Testing of Microbicidal Activity

In this method, microbicidal activity was determined from spawn growth rate. Six common microbes associated with commercial crops, vegetable crops and fruit crops were selected as targets for testing: Rice Sheath Blight Disease, gray mold of cucumber, wheat scab, early blight of tomato, Tobacco brown spot and anthracnose of cucumber. The compounds were dissolved in a small amount of acetone, emulsified with Tween-80, and added with distilled water to achieve given concentrations for use. 200 grams (g) potato, 15 g glucose, 15 g agar and 1000 g water were formulated into a culture medium, and sterilized with dishes having a diameter of 9 cm at high temperature and at reduced pressure for 25 minutes. Then 13.5 mL hot medium and 1.5 mL prepared compound solution were mixed uniformly and distributed equally into two dishes. The dishes were placed levelly, and after cooling, 5 mm agar with microbes collected from the culture of strains was inoculated into each dish by a sterile collector. Surface of spawn faces downward and each dish was placed with 2-3 strains. Two blank control groups were established. The dishes were then placed into a sterile, constant temperature drying oven for 48 hours. Diameters of the bacterial plaque were measured. Based on plaque diameter of the control, the efficacy of compounds is indicated by the diameters:

Inhibition %=(control−treatment)/control×100%.

Testing materials: strains: wheat scab (*Gibberella zeae*), gray mold of cucumber (*Botrytis cinerea*), early blight of tomato (*Alternaria solania*), tobacco brown spot (*Alternaria alternate* (Fries) Keissler), anthracnose of cucumber (GloeosporiumorbiculareArs). Testing results were given in table 4-8.

TABLE 4

Testing results from some compounds
(testing concentration of 100 μg/g)

| Compound No. | Gray mold of cucumber Average inhibition rate (%) | Compound No. | Tobacco brown spot Average inhibition rate (%) |
|---|---|---|---|
| 2 | 73 | 2 | 52 |
| 3 | 70 | 4 | 66 |
| 4 | 77 | 5 | 56 |
| 5 | 67 | 7 | 57 |
| 6 | 63 | 10 | 58 |
| 7 | 67 | 14 | 60 |
| 8 | 54 | 32 | 87 |
| 9 | 79 | 35 | 75 |
| 10 | 56 | 39 | 50 |
| 11 | 67 | | |
| 12 | 53 | | |
| 13 | 49 | | |
| 14 | 54 | | |
| 15 | 44 | | |
| 16 | 82 | | |

TABLE 4-continued

Testing results from some compounds
(testing concentration of 100 μg/g)

| Compound No. | Gray mold of cucumber Average inhibition rate (%) | Compound No. | Tobacco brown spot Average inhibition rate (%) |
|---|---|---|---|
| 32 | 59 | | |
| 33 | 61 | | |
| 34 | 63 | | |
| 35 | 49 | | |
| 36 | 61 | | |
| 37 | 98 | | |
| 38 | 61 | | |
| 39 | 84 | | |
| Difenoconazole | 73 | | |

TABLE 5

Testing results from some compounds
(testing concentration of 100 μg/g)

| Compound No. | Anthracnose of cucumber Average inhibition rate (%) | Compound No. | Wheat scab Average inhibition rate (%) | Compound No. | Early blight of tomato Average inhibition rate (%) |
|---|---|---|---|---|---|
| 2 | 50 | 2 | 51 | 4 | 51 |
| 4 | 65 | 11 | 54 | 32 | 63 |
| 10 | 64 | 16 | 63 | | |
| 15 | 57 | 33 | 55 | | |
| 32 | 67 | 34 | 51 | | |
| 35 | 50 | 37 | 51 | | |
| 38 | 54 | 38 | 56 | | |
| 39 | 52 | | | | |

TABLE 6

Testing results from some compounds
(testing concentration of 100 μg/g)

| Compound No. | Wheat scab Average inhibition rate (%) | Sheath and culm blight of rice Average inhibition rate (%) | Gray mold of cucumber Average inhibition rate (%) | Early blight of tomato Average inhibition rate (%) |
|---|---|---|---|---|
| 23 | 59 | 96 | 88 | 57 |
| 24 | 68 | 97 | 84 | 66 |
| 25 | 62 | 97 | 96 | 71 |
| 26 | 55 | 99 | 92 | 69 |
| 27 | 39 | 94 | 99 | 38 |
| 28 | 67 | 100 | 100 | 69 |
| 29 | 67 | 98 | 100 | 60 |
| 31 | 58 | 97 | 95 | 70 |
| 82 | 48 | 96 | 96 | 70 |
| 84 | 62 | 98 | 93 | 58 |
| 86 | 62 | 99 | 100 | 60 |
| Difenoconazole | 98 | 100 | 96 | 100 |

TABLE 7

Testing results from some compounds

| Compound No. | Concentration (μg/g) | Wheat scab | Sheath and culm blight of rice | Gray mold of cucumber | Early blight of tomato |
|---|---|---|---|---|---|
| 28 | 25 | 43 | 91 | 42 | 0 |
| | 50 | 64 | 98 | 86 | 28 |
| | 100 | 69 | 99 | 90 | 68 |
| 29 | 25 | 26 | 64 | 79 | 0 |
| | 50 | 45 | 70 | 90 | 25 |
| | 100 | 52 | 96 | 100 | 41 |
| Difenoconazole | 100 | 95 | 91 | 86 | 100 |

TABLE 8

Testing results from some compounds

| No. | Concentration (μg/g) | Sheath and culm blight of rice | Gray mold of cucumber |
|---|---|---|---|
| 25 | 50 | 61 | 67 |
| | 25 | 25 | 50 |
| | 12.5 | 0 | 40 |
| 26 | 50 | 94 | 88 |
| | 25 | 72 | 55 |
| | 12.5 | 58 | 43 |
| 27 | 50 | 72 | 92 |
| | 25 | 37 | 66 |
| | 12.5 | 0 | 59 |
| 28 | 50 | 98 | 98 |
| | 25 | 96 | 90 |
| | 12.5 | 87 | 85 |
| 29 | 50 | 69 | 91 |
| | 25 | 68 | 72 |
| | 12.5 | 33 | 47 |
| 31 | 50 | 96 | 91 |
| | 25 | 88 | 87 |
| | 12.5 | 78 | 75 |
| 82 | 50 | 100 | 99 |
| | 25 | 90 | 97 |
| | 12.5 | 63 | 56 |
| 84 | 50 | 97 | 94 |
| | 25 | 95 | 90 |
| | 12.5 | 73 | 66 |
| 86 | 50 | 98 | 97 |
| | 25 | 74 | 76 |
| | 12.5 | 37 | 40 |
| Difenoconazole | 100 | 100 | 96 |

While there has been shown several and alternate embodiments of the present invention, it is to be understood that certain changes can be made as would be known to one skilled in the art without departing from the underlying scope of the present invention as is discussed and set forth above and below including claims. Furthermore, the embodiments described above and claims set forth below are only intended to illustrate the principles of the present invention and are not intended to limit the scope of the present invention to the disclosed elements.

What is claimed is:

1. A 2-methyl-4-amino-5-(substituted-1H-1,2,3-triazolyl)methylpyrimidine compound, having a structure of formula I:

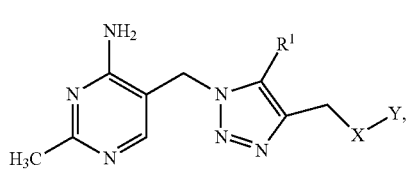

wherein $R^1$ represents hydrogen or iodine, X represents O or NH, Y represents phenyl or substituted phenyl, benzoyl or substituted benzoyl, phenoxyacetyl or substituted phenoxyacetyl; and wherein each substituent on the benzene ring of Y is H, halogen, nitro, cyano, $CF_3$, $C_{1-4}$ alkyl, methoxy, $C_{1-2}$ carboxy or alkoxycarbonyl, the substituents are mono- or multi-substituted at any position of the benzene ring, and the substituents are the same or different.

2. A method for preparing the 2-methyl-4-amino-5-(substituted-1H-1,2,3-triazolyl)methylpyrimidine compound of claim 1, wherein the 2-methyl-4-amino-5-(substituted-1H-1,2,3-triazolyl)methylpyrimidine compound has a structure of formula I-1;

wherein the structure of formula I-1 is prepared by reacting a compound of formula II with a compound of formula III:

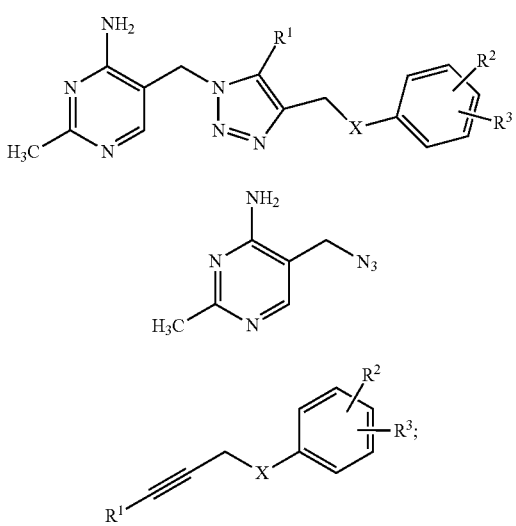

and wherein in formula I-1 and formula III, $R^1$ is defined as in formula I, $R^2$ is H, halogen, nitro or $C_{1-4}$ alkyl, and $R^3$ is H, halogen, nitro, cyano, $CF_3$, $C_{1-4}$ alkyl, methoxy, $C_{1-2}$ carboxy or carboxylate alkoxycarbonyl.

3. A method for preparing the 2-methyl-4-amino-5-(substituted-1H-1,2,3-triazolyl)methylpyrimidine compound of claim 1, wherein the 2-methyl-4-amino-5-(substituted-1H-1,2,3-triazolyl)methylpyrimidine compound has a structure of formula I-2;

wherein the structure of formula I-2 is prepared by reacting a compound of formula II with a compound of formula IV:

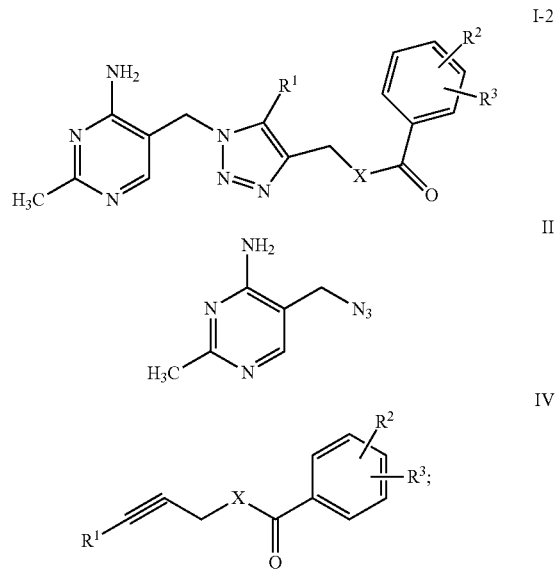

and wherein in formula I-2 and formula IV, X is defined as in formula I, $R^1$ represents hydrogen or iodine, $R^2$ is H, halogen or nitro, and $R^3$ is H, halogen, nitro or $C_{1-4}$ alkyl.

4. A method for preparing the 2-methyl-4-amino-5-(substituted-1H-1,2,3-triazolyl)methylpyrimidine compound of claim 1, wherein the 2-methyl-4-amino-5-(substituted-1H-1,2,3-triazolyl)methylpyrimidine compound has a structure of formula I-3;

wherein the structure of formula I-3 is prepared by reacting a compound of formula II with a compound of formula V:

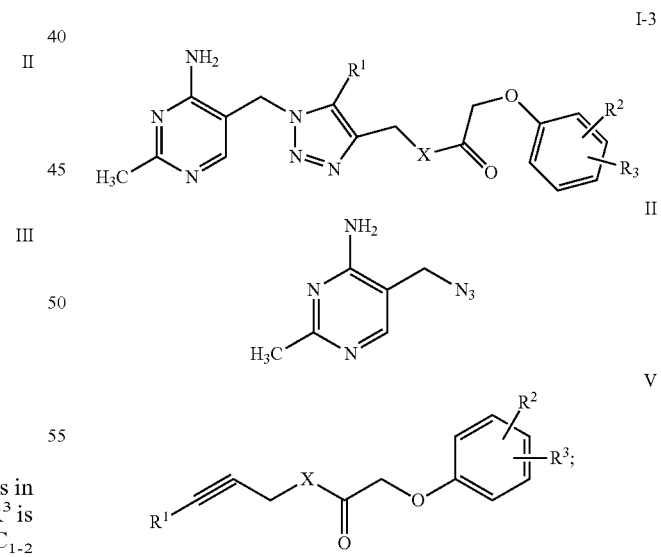

and wherein in formula I-3 and formula V, X is defined as in formula I, $R^1$ represents hydrogen, $R^2$ is H, halogen, nitro, $CF_3$ or $C_{1-4}$ alkyl, and $R^3$ is H, halogen, nitro, $C_{1-4}$ alkyl or methoxy.

* * * * *